United States Patent
Dong et al.

(10) Patent No.: US 11,759,417 B2
(45) Date of Patent: Sep. 19, 2023

(54) PHARMACEUTICAL COMPOSITION AND PREPARATION METHOD THEREFOR AND USE THEREOF

(71) Applicant: SHANGHAI WD PHARMACEUTICAL CO., LTD, Shanghai (CN)

(72) Inventors: Liang Chang Dong, Shanghai (CN); Xishan Chen, Shanghai (CN)

(73) Assignee: SHANGHAI WD PHARMACEUTICAL CO., LTD, Shanghai (CN)

(*) Notice: Subject to any disclaimer, the term of this patent is extended or adjusted under 35 U.S.C. 154(b) by 122 days.

(21) Appl. No.: 16/976,038

(22) PCT Filed: Feb. 28, 2019

(86) PCT No.: PCT/CN2019/076491
§ 371 (c)(1),
(2) Date: Aug. 26, 2020

(87) PCT Pub. No.: WO2019/165993
PCT Pub. Date: Sep. 6, 2019

(65) Prior Publication Data
US 2021/0015737 A1   Jan. 21, 2021

(30) Foreign Application Priority Data
Feb. 28, 2018 (CN) .......................... 201810166976.4

(51) Int. Cl.
| A61K 9/00 | (2006.01) |
| A61K 9/20 | (2006.01) |
| A61K 9/28 | (2006.01) |
| A61K 31/155 | (2006.01) |
| A61K 31/197 | (2006.01) |
| A61K 31/198 | (2006.01) |
| A61K 31/522 | (2006.01) |
| A61K 47/32 | (2006.01) |

(52) U.S. Cl.
CPC .......... *A61K 9/0004* (2013.01); *A61K 9/2086* (2013.01); *A61K 9/2893* (2013.01); *A61K 31/155* (2013.01); *A61K 31/197* (2013.01); *A61K 31/198* (2013.01); *A61K 31/522* (2013.01); *A61K 47/32* (2013.01)

(58) Field of Classification Search
None
See application file for complete search history.

(56) References Cited

U.S. PATENT DOCUMENTS

| 3,845,770 A | 11/1974 | Theeuwes et al. |
| 3,916,899 A | 11/1975 | Theeuwes et al. |
| 4,327,725 A | 5/1982 | Cortese et al. |
| 4,612,008 A | 9/1986 | Wong et al. |
| 5,200,195 A | 4/1993 | Dong et al. |
| 5,869,096 A | 2/1999 | Barclay et al. |
| 8,377,474 B2 | 2/2013 | Hsu et al. |
| 8,454,998 B2 | 6/2013 | Hsu et al. |
| 8,557,283 B2 | 10/2013 | Hsu et al. |
| 9,089,607 B2 | 7/2015 | Hsu et al. |
| 9,089,608 B2 | 7/2015 | Hsu et al. |
| 10,098,845 B2 | 10/2018 | Hsu et al. |
| 2016/0243036 A1 | 8/2016 | Paiement et al. |

FOREIGN PATENT DOCUMENTS

| CN | 102293760 | * 12/2011 |
| CN | 102293760 A1 | 12/2011 |
| CN | 105658211 A1 | 6/2016 |
| EP | 3797818 A1 | 3/2021 |
| JP | 2016532655 A | * 10/2016 |
| JP | 2016532655 A | 10/2016 |
| WO | 2015054302 A1 | 4/2015 |
| WO | 2019223753 A1 | 11/2019 |

OTHER PUBLICATIONS

Keraliya et al. (Osmotic Drug Delivery System as a part of Modified Release Dosage Form, ISRN Pharm 2012). (Year: 2012).*
Extended European Search Report dated Apr. 1, 2021 issued in EP Application No. 19760782.3, 8 pages.
Anonymous: "Aqualon CMC, Product Grades Available," Jan. 1, 2016, XP055492100, Retrieved from the Internet: URL:https://www.ashland.com/file_source/Ashland/Industries/Pharmaceutical/Articles/PC-11608.11_Pharma_Product_Grades.pdf [retrieved on Jul. 12, 2018, 4 pages.
International Search Report dated Jun. 3, 2019 issued in International Application No. PCT/CN2019/076491, with English translation, 8 pages.
Written Opinion dated Jun. 3, 2019 issued in International Application No. PCT/CN2019/076491, with English translation, 12 pages.
Luo, Mingsheng, et al., "Non-official translation: Copovidone", Non-official translation: Encyclopedia of Supplementary Agents, Jan. 31, 2006, SBN 7-5364-2397-7, p. 1002, left-hand column, lines 13-20.
Notice of Reasons for Refusal dated Oct. 26, 2021 issued in JP Application No. 2020-545314, with English translation, 7 pages.

(Continued)

*Primary Examiner* — Melissa S Mercier
(74) *Attorney, Agent, or Firm* — FOLEY & LARDNER LLP

(57) ABSTRACT

Disclosed are a pharmaceutical composition, an osmotic pump controlled-release drug delivery system comprising the pharmaceutical composition and a preparation method therefor. The pharmaceutical composition comprises a tablet core and a coating film. The tablet core comprises a drug-pulling layer, and the coating film comprises 50-90 wt % of cellulose acetate and 10-50 wt % of Copovidone. The Copovidone can be obtained by means of the polymerization of vinyl pyrrolidone and vinyl acetate in a molar ratio of 40:60-80:20.

21 Claims, 6 Drawing Sheets

(56) References Cited

OTHER PUBLICATIONS

First Office Action dated Oct. 13, 2021 issued in CN Application No. 201980006955.9, with English translation, 10 pages.
Communication pursuant to Article 94(3) EPC dated Feb. 16, 2023 issued in European Patent Application No. 19 760 782.3, 5 pages.

* cited by examiner

PHARMACEUTICAL COMPOSITION AND PREPARATION METHOD THEREFOR AND USE THEREOF

This application is a 371 of PCT/CN2019/076491, filed Feb. 28, 2019, which claims priority to Chinese Patent Application No. CN201810166976.4 filed on Feb. 28, 2018, the contents of which are incorporated herein by reference in their entireties.

FIELD OF INVENTION

The present invention relates to the field of biomedicine, specifically relates to a pharmaceutical composition and a preparation method therefor and use thereof.

PRIOR ARTS

A great number of active pharmaceutical ingredients (APIs) including levodopa, baclofen, acyclovir, valacyclovir, ganciclovir, metformin, gabapentin and others, have their absorption window limited at the upper gastrointestinal tract (UGIT). Incorporation of such APIs with conventional extended release dosages, will not only result in compromised bioavailability, but also leads to failure of achieving prolonged therapeutic coverage. Therefore, a number of technologies have been disclosed in the prior art to extend the retention time in the stomach. Following are these technologies: expansion, swelling, floating, raft formation, sinking and mucosal adhesion. These aforementioned technologies have very limited success, especially when the oral dosage forms obtained by using these technologies are administered at fasting state. Therefore, there is a need for a novel controlled-release drug delivery system that can provide prolonged release of these APIs with their absorption window limited at the UGIT.

One of such APIs is levodopa used for the treatment of Parkinson's disease (PD). PD is a progressive disease which results from the loss of dopamine-producing cells in the brain. Dopamine is a substance that is naturally present in the brain and spinal cord, which helps nerve cells in the brain to properly control motor functions. As the level of dopamine in the brain decreases, symptoms of PD would occur, such as muscle stiffness, slow movements and difficulty in keeping one's balance. Dopamine can't penetrate the blood-brain barrier (BBB), which is the reason why oral dosage form of dopamine does not work. Levodopa (LD) is a precursor of dopamine, which can pass through the BBB and can be transformed to dopamine in brain tissue. Levodopa therapy is still a "gold standard" for treatment of Parkinson's disease, and nearly all PD patients receive LD treatment at some stage of the disease. However, most levodopa is decarboxylated to dopamine before reaching the brain. For this reason, LD is usually administered with a decarboxylase inhibitor such as Carbidopa (CD) or benserazide to prevent formation of peripheral dopamine. Treatment with LD/CD may increase the amount of dopamine in the brain and reduce the PD symptoms.

Despite oral administration of LD medications, patients often develop motor complications in the form of fluctuations (so-called "on-off" phenomena and involuntary movement (dyskinesia)). The cause of the fluctuation can be attributed to non-physiological pulsation stimulation of postsynaptic dopamine receptors in the striatum as a result of the short half-life of LD. In addition, the therapeutic window is becoming narrower as the PD is progressing, implying that patients with advanced PD are more susceptible to akinesia (movement freezing) and dyskinesia.

Theoretically, an extended release oral dosage forms could provide with a steady LD plasma concentration to prolong therapeutic coverage, thereby alleviating the "on-off" phenomena. In reality, it's a great challenge to develop an extended release LD dosage form, since its absorption at the proximal gastrointestinal tract (GI tract). The residence time of a dosage form at the proximal GI tract is approximately 3-4 hours. Any amount of LD that is released for more than 3-4 hours will not be absorbed and ends up in fecal material. U.S. Pat. Nos. 9,809,607, 9,089,608, 8,557,283, 8,454,998 and 8,377,474 disclose the use of organic acids to prolong the absorption time of LD, resulting in an extended release dosage form with absorption duration of approximately 4 to 5 hours. Rytary is the product using the formulation protected by these patents, which is suitable for treatment of early and moderate PD.

Treatment of patients with advanced PD remains a medical challenge. Currently, Deep Brain Stimulation (DBS) and continuous intestinal LD infusion to the duodenum (DUOPA) are the treatment for advanced PD patients who have experienced unsatisfactory effect with oral dosage forms. Since DBS involves a brain surgery, this treatment is very invasive, usually intimidating most patients. In addition, DBS also carries a risk of neuropsychological side effects. DUOPA comprises a gel formulation that is administered with a pump via a tube, directly into the upper small intestine throughout the day. Continuous intestinal LD infusion to the duodenum can maintain consistent LD plasma levels over 16 hours, providing a more sustained stimulation of the dopamine receptors and thereby reducing motor and non-motor complications associated with pulsatile dopaminergic stimulation produced by current oral medications.

However, DUOPA therapy is also very invasive, which requires a surgical procedure or percutaneous endoscopic gastrostomy for the placement of tubes to the duodenum. For some patients, the accompanying pump can be cumbersome. Other problems may also occur, including sporadic blockage of tubes, displacement of the inner tube, leakage at the tube joints and local infections. In addition, the formulation of DUOPA gel is unstable, and it must be stored in a refrigerator (2° C.-8° C.) to minimize the degradation of products, especially hydrazine, that is known to be genotoxic and possibly carcinogenic. Even at the refrigerated conditions, the shelf life of the product is still very short, only 15 weeks. Finally, high costs may be a limiting factor. Treatment with DUOPA is expensive and requires an expert team comprising neurologists, gastroenterologists and nurses, as well as an outbound liaison to cooperate in the care of patients. Therefore, it is necessary to provide a pharmaceutical composition, which is capable of increasing the absorption window, to provide a non-invasive controlled-release product that can provide a steady LD plasma profile for treatment of PD patients, especially advanced ones.

In addition, in manufacturing the osmotic pump tablets, there is a potential problem of cellulose acetate precipitation during the membrane coating. The membrane completely or at least partially comprises a semi-permeable polymer that is permeable to water or moisture present in the oral cavity, while substantially impermeable to drugs and other optional ingredients that possibly present in the tablet core. A representative semi-permeable polymer is cellulose acetate with an acetyl content of 32.0-39.8%. A flux enhancer can be incorporated into the rate control membrane. In the prior art, the flux enhancer comprises, but is not limited to, polyethylene glycol, Povidone and other water-soluble polymers. In the prior art, water-soluble polymers of semi-permeable membrane generally use polyethylene glycol (PEG) or Povidone (PVP) or the like in combination with cellulose acetate. As water-soluble polymers, PEG and PVP are both soluble in water but insoluble in acetone, therefore, the solvent is generally a mixture of acetone and water, such as 90% acetone+10% water. When the dose strength of the osmotic pump tablet is high and the size of tablet core is also large, a higher proportion of PEG or PVP is required if fast release of APIs is necessitated. There are significant differences in evaporation rates between acetone and cellulose acetate, or water and flux-enhancer, especially at low temperatures, which often leads to unknown incompatibilities, that is, cellulose acetate may precipitate during the membrane coating process. Therefore, the solvents in the prior art often produce high-throughput membranes with mechanical defects, that is, membranes with reduced mechanical strength, opaque, or even white, leading to uneven coating, unstable drug release and even rupture of the membrane during release.

CONTENT OF THE PRESENT INVENTION

The technical problems to be solved in the present invention is that the current controlled-release drugs cannot provide a long-term and stable plasma profile of active pharmaceutical ingredients; in addition, cellulose acetate precipitates from the coating membrane of the drug, the coating is uneven, and the drug release is unstable.

In order to solve the above technical problems, in one aspect of the technical solutions, the present invention provides a pharmaceutical composition comprising a tablet core and a coating membrane, wherein the tablet core comprises a drug pull-layer, and the coating membrane comprises cellulose acetate and Copovidone, the weight of the cellulose acetate is 50-90% of the weight of the coating membrane; the weight of the Copovidone is 10-50% of the weight of the coating membrane; wherein, the Copovidone is prepared by the following method including the following steps: polymerizing vinyl pyrrolidone and vinyl acetate, wherein the weight ratio of the vinyl pyrrolidone and vinyl acetate is 40:60-80:20. The position relationship between the tablet core and the coating membrane is that the tablet core is coated with the coating membrane. The pharmaceutical composition may be one of osmotic pump controlled-release drug delivery systems, that is, a single-layer elementary osmotic pump.

The osmotic controlled-release drug delivery system is an advanced oral osmotic pump controlled-release drug delivery system in the form of a tablet with a semi-permeable outer membrane and one or more small laser-drilled orifices. When the tablet is taken orally through the gastrointestinal tract, water is absorbed through the semi-permeable membrane through osmosis, and the resulting osmotic pressure will push the active drug through the orifice of the tablet. Elementary Osmotic Pump (EOP) was developed by ALZA in 1974, which is the first example of an oral osmotic pump drug delivery system. It is comprised of a drug-containing tablet core coated with a semi-permeable coating membrane, and an orifice drilled for drug release on the coating membrane, so that the osmotic pump preparation can be simplified into the form of an ordinary coated tablet. Push-Pull Osmotic Pump (PPOP) is suitable for soluble or poorly soluble drugs, which can be a bi-layer tablet with a semi-permeable membrane. A drug pull-layer comprises a drug chamber containing drugs and osmotic active substance, and an osmotic push-layer comprises osmotic polymers. When the system contacts with the water environment, the osmotic push-layer swells and pushes the drugs in the drug chamber to release through the drug delivery orifice. The pharmaceutical composition or Upper Gastrointestinal controlled-release drug delivery system (UGI Pump) in the present invention comprises the forms of a single-layer elementary osmotic pump, a bi-layer push-pull osmotic pump, and a bi-layer push-pull osmotic pump comprising an immediate-release drug overcoat (the overcoat), etc., but differs from the osmotic pump of the prior art.

Preferably, the drug pull-layer comprises active pharmaceutical ingredients and excipients, and the active pharmaceutical ingredients are one or more of levodopa, carbidopa, baclofen, acyclovir, valacyclovir, ganciclovir, metformin and gabapentin; in the preparation method for the Copovidone, wherein the weight ratio of the vinyl pyrrolidone and the vinyl acetate is 50:50-70:30.

Preferably, the molar ratio of the vinyl pyrrolidone to the vinyl acetate is 60:40 in the method for preparing the Copovidone; the active pharmaceutical ingredients comprise levodopa and/or carbidopa; and/or, the excipients are one or more of a filler, an osmotic agent, a hydrophilic polymer, a binding agent, a lubricant, a preservative, a flavoring agent, an acidifying agent and an antioxidant. More preferably, the excipients are one or more of a filler, an osmotic agent, a hydrophilic polymer, a binding agent, a lubricant and a preservative. Even more preferably, the excipients are a filler, an osmotic agent, a hydrophilic polymer, a binding agent, a lubricant and a preservative.

Preferably, when the pharmaceutically active ingredients comprise levodopa, the weight percentage of the levodopa is 20-70%; when the active ingredients comprise carbidopa, the weight percentage of the carbidopa is 0-20% but not 0%; wherein the weight percentage is the weight percentage of each component of the drug pull-layer.

More preferably, when the pharmaceutically active ingredients comprise levodopa, the weight percentage of the levodopa is 35-55%; when the active ingredients comprise carbidopa, the weight percentage of the carbidopa is 5-15%; wherein the weight percentage is the weight percentage of each component of the drug pull-layer.

Preferably, in the above pharmaceutical composition, when the excipients comprise a filler, the filler is one or more of microcrystalline cellulose, hydroxypropyl cellulose and mannitol, wherein the weight percentage of the filler is 0-50% but not 0%;

When the excipients comprise an osmotic agent, the osmotic agent is one or more of magnesium sulfate, magnesium chloride, sodium chloride, lithium chloride, potassium sulfate, sodium sulfate, mannitol, urea, sorbitol, inositol, sucrose and glucose, wherein the weight percentage of the osmotic agent is 0-50% but not 0%;

When the excipients comprise a hydrophilic polymer, the hydrophilic polymer is one or more of hydroxypropyl cellulose, hydroxypropyl methylcellulose, carboxymethyl cellulose, polyvinylpyrrolidone and hydroxyethyl cellulose, wherein the weight percentage of the hydrophilic polymer is 0-50% but not 0%;

When the excipients comprise an acidifying agent, the acidifying agent is one or more of citric acid, sodium citrate, potassium citrate, malic acid, fumaric acid, lactic acid, phosphoric acid and tartaric acid, wherein the weight percentage of the acidifying agent is 0-10% but not 0%;

The weight percentage thereof is the weight percentage of each component of the drug pull-layer.

In order to solve the above technical problems, in one aspect of the technical solutions, the present invention provides an aforementioned pharmaceutical composition, wherein the tablet core further comprises an osmotic push-layer comprising a hydrophilic polymer, an osmotic agent and a binding agent. Preferably, the osmotic push-layer comprises a hydrophilic polymer, an osmotic agent, a binding agent and a lubricant. More preferably, the osmotic push-layer comprises a hydrophilic polymer, an osmotic agent, a binding agent, a lubricant and a colorant. The osmotic push-layer and the drug pull-layer are the components of a bi-layer tablet core, and the position relationship between the bi-layer tablet core and the coating membrane is that the tablet core is coated with the coating membrane. The pharmaceutical composition may be one of osmotic pump controlled-release drug delivery system, that is, a bi-layer push-pull osmotic pump.

As a pharmaceutical composition of the bi-layer push-pull osmotic pump, preferably, the hydrophilic polymer of the osmotic push-layer is κ-carrageenan, sodium carboxymethyl cellulose or polyethylene oxide, and the molecular weight of the hydrophilic polymer is 75,000-7,500,000, wherein the weight percentage of the hydrophilic polymer is 25-85%;

The osmotic agent of the osmotic push-layer is one or more of magnesium sulfate, magnesium chloride, sodium chloride, lithium chloride, potassium sulfate, sodium sulfate, mannitol, urea, sorbitol, inositol, sucrose and glucose, wherein the weight percentage of the osmotic agent is 5-65%;

When the osmotic push-layer comprises a binding agent, the binding agent is one or more of methyl cellulose, hydroxypropyl methylcellulose, hydroxypropyl cellulose, sodium carboxymethyl cellulose, Povidone and gelatin, wherein the weight percentage of the binding agent is 3-20%;

When the osmotic push-layer comprises a lubricant, the lubricant is one or more of magnesium stearate, magnesium stearate fumarate, talc and colloidal silica, wherein the weight percentage of the lubricant is 0-2% but not 0%;

And/or, when the osmotic push-layer comprises a colorant, the colorant is one or more of iron oxide red, iron oxide yellow and iron oxide black, wherein the weight percentage of the colorant is 0-5% but not 0%;

The weight percentage thereof is the weight percentage of each component of the osmotic push-layer.

Preferably, the osmotic push-layer comprises sodium carboxymethyl cellulose, sorbitol, Povidone, iron oxide red and magnesium stearate; or sodium carboxymethyl cellulose, hydroxypropyl cellulose, sorbitol, iron oxide red and magnesium stearate; preferably is composed of sodium carboxymethyl cellulose, Povidone K30, sorbitol, iron oxide red and magnesium stearate; or sodium carboxymethyl cellulose, hydroxypropyl cellulose, sorbitol, iron oxide red and magnesium stearate; more preferably, the sodium carboxymethyl cellulose is sodium carboxymethyl cellulose 7H4XF or 9H4XF; even more preferably, the osmotic push-layer comprises, in weight percentage, 25-85 Wt % of sodium carboxymethyl cellulose, 5-65 Wt % of sorbitol, 3-20 Wt % of Povidone, 0-5 Wt % of iron oxide red and 0.5-2 Wt % of magnesium stearate; or 25-85 Wt % of sodium carboxymethyl cellulose, 5-65 Wt % of sorbitol, 3-20 Wt % of hydroxypropyl cellulose, 0-5 Wt % of iron oxide red and 0.5-2 Wt % of magnesium stearate; wherein the weight percentage is the weight percentage of each component of the osmotic push-layer.

In order to solve the above technical problems, in one aspect of the technical solutions, the present invention provides an aforementioned pharmaceutical composition, wherein the coating membrane is further covered with an overcoat. Thus, a three-layer structure is formed: the inner layer is the tablet core, the middle layer is the coating membrane, and the outer layer is the overcoat.

Preferably, the overcoat comprises active pharmaceutical ingredients and excipients, the active pharmaceutical ingredients comprise levodopa and/or carbidopa, the excipients are one or more of hydroxypropyl cellulose, aspartame and Mint flavor.

More preferably, when the active pharmaceutical ingredient is levodopa, the weight percentage of the levodopa is 0-75% but not 0%; when the active pharmaceutical ingredient is carbidopa, the weight percentage of carbidopa is 0-93% but not 0%; when the excipient of the overcoat comprises hydroxypropyl cellulose, the weight percentage of hydroxypropyl cellulose is 2-20%; when the excipient of the overcoat comprises aspartame, the weight percentage of the aspartame is 0-5%; when the excipient of the overcoat comprises Mint flavor, the weight percentage of the Mint flavor is 0-5%; wherein the weight percentage is the weight percentage of each component of the overcoat.

Even more preferably, the weight of the coating membrane is not less than 2.0% of the weight of tablet core; the coating membrane has one or more exit orifices, the diameter of the exit orifice is preferably 0.5 mm-1.0 mm, more preferably 0.5 mm, 0.75 mm and 1.0 mm. Preferably, the weight of the coating membrane is 2.0-15.0% of the weight of the tablet core. More preferably, the weight of the coating membrane is 4.0-8.0% of the weight of the tablet core.

Preferably, the present invention provides an aforementioned pharmaceutical composition, wherein the pharmaceutical composition is composed of a drug pull-layer and a coating membrane; or a drug pull-layer, an osmotic push-layer and a coating membrane; or a drug pull-layer, an osmotic push-layer, a coating membrane and an overcoat.

Preferably, the drug pull-layer comprises levodopa, carbidopa, microcrystalline cellulose, mannitol, citric acid, sodium hydroxypropyl methylcellulose and magnesium stearate; or levodopa, microcrystalline cellulose, hydroxypropyl methylcellulose and magnesium stearate; or levodopa, carbidopa, mannitol, citric acid and magnesium stearate; or levodopa, carbidopa, hydroxypropyl cellulose, mannitol, citric acid and magnesium stearate; or levodopa, carbidopa, hydroxypropyl cellulose, mannitol, citric acid and Povidone K30; or levodopa, hydroxypropyl cellulose, mannitol, Povidone K30, magnesium stearate, Mint flavor and aspartame; or levodopa, mannitol, Povidone K30 and magnesium stearate; or levodopa, carbidopa, hydroxypropyl cellulose, mannitol, aspartame and magnesium stearate; or levodopa, hydroxypropyl cellulose, mannitol, magnesium stearate, Mint flavor and aspartame; or levodopa, hydroxypropyl cellulose, mannitol, Povidone K30, magnesium stearate and aspartame;

The osmotic push-layer comprises sodium carboxymethyl cellulose, Povidone K30, sorbitol, iron oxide red and magnesium stearate; or sodium carboxymethyl cellulose, hydroxypropyl cellulose, sorbitol, iron oxide red and magnesium stearate; preferably, the sodium carboxymethyl cellulose is sodium carboxymethyl cellulose 7H4XF or 9H4XF;

And/or, the overcoat comprises levodopa, carbidopa, hydroxypropyl cellulose, aspartame and Mint flavor; or levodopa, carbidopa, hydroxypropyl cellulose and aspartame; or carbidopa, hydroxypropyl cellulose and aspartame; or levodopa, hydroxypropyl cellulose and Mint flavor. As is known to those skilled in the art, the above "comprise" can be replaced by "be composed of".

Preferably, when the drug pull-layer is composed of levodopa, carbidopa, microcrystalline cellulose, mannitol, citric acid, sodium hydroxypropyl methylcellulose and magnesium stearate, the weight percentage of the levodopa is 40%, the weight percentage of the carbidopa is 10.8%, the weight percentage of the microcrystalline cellulose is 20%, the weight percentage of the mannitol is 18.7%, the weight percentage of the citric acid is 5%, the weight percentage of the sodium hydroxypropyl methylcellulose is 5%, and the weight percentage of the magnesium stearate is 0.5%, wherein the weight percentage is the weight percentage of each component of the drug pull-layer;

When the drug pull-layer is composed of levodopa, microcrystalline cellulose, hydroxypropyl methylcellulose and magnesium stearate, the weight percentage of the levodopa is 38%, the weight percentage of the microcrystalline cellulose is 50%, the weight percentage of the hydroxypropyl methylcellulose is 10%, and the weight percentage of the magnesium stearate is 2%, wherein the weight percentage is the weight percentage of each component of the drug pull-layer;

When the drug pull-layer is composed of levodopa, carbidopa, mannitol, citric acid and magnesium stearate, the weight percentage of the levodopa is 19.5%, the weight percentage of the carbidopa is 20%, the weight percentage of the mannitol is 50%, the weight percentage of the citric acid is 10%, and the weight percentage of magnesium stearate is 0.5%, wherein the weight percentage is the weight percentage of each component of the drug pull-layer;

When the drug pull-layer is composed of levodopa, carbidopa, hydroxypropyl cellulose, mannitol, citric acid and magnesium stearate, the weight percentage of the levodopa is 40%, the weight percentage of the carbidopa is 10.8%, the weight percentage of the hydroxypropyl cellulose is 31%, the weight percentage of the mannitol is 12.7%, the weight percentage of the citric acid is 5%, and the weight percentage of the magnesium stearate is 0.5%, wherein the weight percentage is the weight percentage of each component of the drug pull-layer;

When the drug pull-layer is composed of levodopa, carbidopa, hydroxypropyl cellulose, mannitol, citric acid and Povidone K30, the weight percentage of the levodopa is 40%, the weight percentage of the carbidopa is 10.8%, the weight percentage of the hydroxypropyl cellulose is 31%, the weight percentage of the mannitol is 12.7%, the weight percentage of the citric acid is 5% and the weight percentage of the Povidone K30 is 0.5%, wherein the weight percentage is the weight percentage of each component of the drug pull-layer;

When the drug pull-layer is composed of levodopa, hydroxypropyl cellulose, mannitol, Povidone K30, magnesium stearate, Mint flavor and aspartame, the weight percentage of the levodopa is 45%, the weight percentage of the hydroxypropyl cellulose is 31%, the weight percentage of the mannitol is 16%, the weight percentage of the Povidone K30 is 5%, the weight percentage of the magnesium stearate is 1%, the weight percentage of the Mint flavor is 1% and the weight percentage of the aspartame is 1%, wherein the weight percentage is the weight percentage of each component of the drug pull-layer;

When the drug pull-layer is composed of levodopa, mannitol, Povidone K30 and magnesium stearate, the weight percentage of levodopa is 70%, the weight percentage of mannitol is 9%, the weight percentage of Povidone K30 is 20%, and the weight percentage of magnesium stearate is 1%, wherein the weight percentage is the weight percentage of each component of the drug pull-layer;

When the drug pull-layer is composed of levodopa, carbidopa, hydroxypropyl cellulose, mannitol, aspartame and magnesium stearate, the weight percentage of the levodopa is 20%, the weight percentage of the carbidopa is 20%, the weight percentage of the hydroxypropyl cellulose is 50%, the weight percentage of the mannitol is 4%, the weight percentage of the aspartame is 5% and the weight percentage of the magnesium stearate is 1%, wherein the weight percentage is the weight percentage of each component of the drug pull-layer;

When the drug pull-layer is composed of levodopa, hydroxypropyl cellulose, mannitol, Povidone K30, magnesium stearate and aspartame, the weight percentage of the levodopa is 45%, the weight percentage of the hydroxypropyl cellulose is 31%, the weight percentage of the mannitol is 17%, the weight percentage of the Povidone K30 is 5%, the weight percentage of the magnesium stearate is 1% and the weight percentage of the aspartame is 1%, wherein the weight percentage is the weight percentage of each component of the drug pull-layer;

When the drug pull-layer is composed of levodopa, hydroxypropyl cellulose, mannitol, Povidone K30, magnesium stearate and aspartame, the weight percentage of the levodopa is 45%, the weight percentage of the hydroxypropyl cellulose is 31%, the weight percentage of the mannitol is 17%, the weight percentage of the Povidone K30 is 5%, the weight percentage of the magnesium stearate is 1% and the weight percentage of the aspartame is 1%, wherein the weight percentage is the weight percentage of each component of the drug pull-layer;

Or, when the drug pull-layer is composed of levodopa, hydroxypropyl cellulose, mannitol, Povidone K30, magnesium stearate, Mint flavor and aspartame, the weight percentage of the levodopa 45%, the weight percentage of the hydroxypropyl cellulose is 31%, the weight percentage of the mannitol is 12%, the weight percentage of the Povidone K30 is 5%, and the weight percentage of the Mint flavor is 5%, the weight percentage of the aspartame is 1% and the weight percentage of the magnesium stearate is 1%, wherein the weight percentage is the weight percentage of each component of the drug pull-layer;

Or, when the drug pull-layer is composed of levodopa, hydroxypropyl cellulose, mannitol, magnesium stearate, Mint flavor and aspartame, the drug pull-layer is composed of 45% weight percentage of levodopa, 31% weight percentage of hydroxypropyl cellulose, 22% weight percentage of mannitol, 0.9% weight percentage of aspartame, 1.0% weight percentage of magnesium stearate and 0.1% weight percentage of Mint flavor; wherein the weight percentage is the weight percentage of each component of the drug pull-layer.

More preferably, the coating membrane is composed of 50% weight percentage of cellulose acetate membrane and 50% weight percentage of Copovidone VA64; the coating membrane is composed of 70% weight percentage of cellulose acetate membrane and 30% weight percentage of Copovidone VA64; the coating membrane is composed weight percentage of 60% cellulose acetate membrane and 40% weight percentage of Copovidone VA64; or the coating membrane is composed of 90% weight percentage of cellulose acetate membrane and 10% weight percentage of Copovidone VA64; wherein the weight percentage is the weight percentage of each component of the coating membrane;

Even more preferably, the weight of the coating membrane is 2.0%, 4.2%, 4.5%, 4.6%, 4.8%, 5.0%, 6.7%, 7.7%, 7.9% or 9.7% of the weight of the tablet core.

Preferably, when the osmotic push-layer is composed of sodium carboxymethyl cellulose 7H4XF, Povidone K30, sorbitol, iron oxide red, and magnesium stearate, the weight percentage of the sodium carboxymethyl cellulose 7H4XF is 55%, the weight percentage of the Povidone K30 is 5%, the weight percentage of sorbitol is 39%, the weight percentage of the iron oxide red is 0.5% and the weight percentage of the magnesium stearate is 0.5%, wherein the weight percentage is the weight percentage of each component of the osmotic push-layer;

the weight percentage of the sodium carboxymethyl cellulose 7H4XF is 55%, the weight percentage of the Povidone K30 is 10%, the weight percentage of the sorbitol is 34%, the weight percentage of the iron oxide red is 0.5% and the weight percentage of the magnesium stearate is 0.5%, wherein the weight percentage is the weight percentage of each component of the osmotic push-layer;

the weight percentage of the sodium carboxymethyl cellulose is 85%, the weight percentage of the Povidone K30 is 3%, the weight percentage of the sorbitol is 5%, the weight percentage of the iron oxide red is 5% and the weight percentage of the magnesium stearate is 2%, wherein the weight percentage is the weight percentage of each component of the osmotic push-layer;

the weight percentage of the sodium carboxymethyl cellulose is 25%, the weight percentage of the Povidone K30 is 9.5%, the weight percentage of the sorbitol is 65% and the weight percentage of the magnesium stearate is 0.5%, wherein the weight percentage is the weight percentage of each component of the osmotic push-layer;

the weight percentage of the sodium carboxymethyl cellulose 7H4XF is 60%, the weight percentage of the Povidone K30 is 10%, the weight percentage of the sorbitol is 26%, the weight percentage of the iron oxide red is 2% and the weight percentage of the magnesium stearate is 2%, wherein the weight percentage is the weight percentage of each component of the osmotic push-layer;

the weight percentage of the sodium carboxymethyl cellulose 7H4XF is 40%, the weight percentage of the Povidone K30 is 20%, the weight percentage of the sorbitol is 36%, the weight percentage of the iron oxide red is 3.5% and the weight percentage of the magnesium stearate is 0.5%, wherein the weight percentage is the weight percentage of each component of the osmotic push-layer;

or, when the osmotic push-layer is composed of sodium carboxymethyl cellulose 9H4XF, Povidone K30, sorbitol, iron oxide red, and magnesium stearate, the weight percentage of the sodium carboxymethyl cellulose 9H4XF is 55%, the weight percentage of the Povidone K30 is 5%, the weight percentage of the sorbitol is 39%, the weight percentage of the iron oxide red is 0.5% and the weight percentage of the magnesium stearate is 0.5%, wherein the weight percentage is the weight percentage of each component of the osmotic push-layer;

or, when the osmotic push-layer is composed of sodium carboxymethyl cellulose 7H4XF, hydroxypropyl cellulose, sorbitol, iron oxide red and magnesium stearate, the weight percentage of the sodium carboxymethyl cellulose is 55%, the weight percentage of the hydroxypropyl cellulose is 10%, the weight percentage of the sorbitol is 34%, the weight percentage of the iron oxide red is 0.5% and the weight percentage of the magnesium stearate is 0.5%, wherein the weight percentage is the weight percentage of each component of the osmotic push-layer.

More preferably, when the overcoat is composed of levodopa, hydroxypropyl cellulose, aspartame and Mint flavor, the weight percentage of the levodopa is 23.78%, the weight percentage of the carbidopa is 64.22%, the weight percentage of the hydroxypropyl cellulose is 10%, the weight percentage of the aspartame is 1% and the weight percentage of Mint flavor is 1%, wherein the weight percentage is the weight percentage of each component of the overcoat;

when the overcoat is composed of carbidopa, hydroxypropyl cellulose and aspartame, the weight percentage of the carbidopa is 93%, the weight percentage of the hydroxypropyl cellulose is 2% and the weight percentage of the aspartame is 5%, wherein the weight percentage is the weight percentage of each component of the overcoat;

when the overcoat is composed of levodopa, hydroxypropyl cellulose and Mint flavor, the weight percentage of the levodopa is 75%, the weight percentage of the hydroxypropyl cellulose is 20% and the weight percentage of the Mint flavor is 5%, wherein the weight percentage is the weight percentage of each component of the overcoat;

when the overcoat is composed of levodopa, carbidopa, hydroxypropyl cellulose and aspartame, the weight percentage of the levodopa is 24%, the weight percentage of the carbidopa is 65%, the weight percentage of the hydroxypropyl cellulose is 10% and the weight percentage of the aspartame is 1%, wherein the weight percentage is the weight percentage of each component of the overcoat;

when the overcoat is composed of levodopa, carbidopa, hydroxypropyl cellulose, aspartame and Mint flavor, the weight percentage of the levodopa is 54%, the weight percentage of the carbidopa is 35%, the weight percentage of the hydroxypropyl cellulose is 10%, the weight percentage of the aspartame is 0.9%, the weight percentage of Mint flavor is 0.1%; or the weight percentage of the levodopa is 42.8%, the weight percentage of the carbidopa is 46.2%, the weight percentage of the hydroxypropyl cellulose is 10%, the weight percentage of the aspartame is 0.9%, the weight percentage of the Mint flavor is 0.1%; or the weight percentage of the levodopa is 28.2%, the weight percentage of the carbidopa is 60.8%, the weight percentage of the hydroxypropyl cellulose is 10%, the weight percentage of the aspartame is 0.9%, the weight percentage of the Mint flavor is 0.1%, wherein the weight percentage is the weight percentage of each component of the overcoat.

Even more preferably, overcoat weight gain relative to the tablet core is 12.9%-13.2%, preferably 12.9%, 13.1% or 13.2% of weight percentage.

In a specific preferred embodiment, the pharmaceutical composition is composed of a drug pull-layer and a coating membrane, wherein the drug pull-layer is composed of 40% weight percentage of levodopa, 10.8% weight percentage of carbidopa, 20% weight percentage of microcrystalline cellulose, 18.7% weight percentage of mannitol, 5% weight percentage of citric acid, 5% weight percentage of sodium hydroxypropyl methylcellulose and 0.5% weight percentage of magnesium stearate, wherein the weight percentage is its weight percentage of the drug pull-layer; the coating membrane is composed of 50% weight percentage of cellulose acetate membrane and 50% weight percentage of Copovidone VA64, the weight percentage is its weight percentage of the coating membrane; wherein the weight of the coating membrane is 2.0% of the weight of the tablet core. The dosage form containing the pharmaceutical composition has a 0.5 mm of exit orifice mechanically drilled on the drug layer side of the coated tablet, and levodopa and carbidopa are delivered at an average rate of 14.17 mg/hr and 4.59 mg/hr, with 85% of the drug delivered in 12 hours and 10 hours, respectively. The dosage form can be kept in oral cavity until the osmotic layer reaches the delivery orifice, or kept there for 8-9 hours before swallowed.

In a specific preferred embodiment, the pharmaceutical composition is composed of a drug pull-layer and a coating membrane, wherein the drug pull-layer is composed of 38% weight percentage of levodopa, 50% weight percentage of microcrystalline cellulose, 10% weight percentage of hydroxypropyl methylcellulose and 2% weight percentage of magnesium stearate, wherein the weight percentage is its weight percentage of the drug pull-layer; the coating membrane is composed of 50% weight percentage of cellulose acetate membrane and 50% weight percentage of Copovidone VA64, wherein the weight percentage is its weight percentage of the coating membrane; and the weight of the coating membrane is 4.5% of the weight of the tablet core. Levodopa is delivered at an average rate of 9.4 mg/hr for the dosage form having a membrane weight gain of 4.5%, with 85% of the levodopa delivered in 9.0 hours.

In a specific preferred embodiment, the pharmaceutical composition is composed of a drug pull-layer and a coating membrane, wherein the drug pull-layer is composed of 19.5% weight percentage of levodopa, 20% weight percentage of carbidopa, 50% weight percentage of mannitol, 10% weight percentage of citric acid and 0.5% weight percentage of magnesium stearate, wherein the weight percentage is its weight percentage of the drug pull-layer; the coating membrane is composed of 50% weight percentage of cellulose acetate membrane and 50% weight percentage of Copovidone VA64, wherein the weight percentage is its weight percentage of the coating membrane; and the weight of the coating membrane is 4.5% of the weight of the tablet core. Levodopa is delivered at an average rate of 22.9 mg/hr for the dosage form having a membrane weight gain of 4.5%, with 85% of the levodopa delivered in 13.0 hours.

In a specific preferred embodiment, the pharmaceutical composition is composed of a drug pull-layer, an osmotic push-layer and a coating membrane, wherein the drug pull-layer is composed of 40% weight percentage of levodopa, 10.8% weight percentage of carbidopa, 31% weight percentage of hydroxypropyl cellulose, 12.7% weight percentage of mannitol, 5% weight percentage of citric acid and 0.5% weight percentage of magnesium stearate; wherein the weight percentage is its weight percentage of the drug pull-layer; the osmotic push-layer is composed of 55% weight percentage of sodium carboxymethyl cellulose 7H4XF or 9H4XF, 5% weight percentage of Povidone K30, 39% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% weight percentage of cellulose acetate membrane and 30% weight percentage of Copovidone VA64, wherein the weight percentage is its weight percentage of the coating membrane; and the weight of the coating membrane is 2.0%, 4.0% or 5.0% of the weight of the tablet core. When sodium carboxymethyl cellulose is 7H4XF, the drug layer comprises an exit orifice of 0.5 mm on the pharmaceutical composition side of the dosage, and dosage form containing the pharmaceutical composition having a coating membrane weight gain of 5.0% of the tablet core delivers levodopa and carbidopa at an average rate of 17.0 mg/hr and 4.6 mg/hr, respectively, with 85% of the drug delivered in 10 hours. The dosage form can be kept in the oral cavity until the osmotic layer reaches the delivery orifice, or kept in the oral cavity for 6-7 hours before swallowed. The size of the delivery orifice varies from 0.5 mm, 0.75 mm, to 1.0 mm, the dosage form containing the pharmaceutical composition having a coating membrane weight gain of 4.0% of the tablet core delivers levodopa and carbidopa at an average rate of 21.3 mg/hr and 5.7 mg/hr, respectively, with 85% of the drug delivered in 8 hours. The dosage form can be kept in the oral cavity until the osmotic layer reaches the delivery orifice, or kept in the oral cavity for 4-5 hours before swallowed. When sodium carboxymethyl cellulose is 9H4XF, the dosage form having a coating membrane weight gain of 2.0% delivers levodopa and carbidopa at an average rate of 24.3 mg/hr and 6.6 mg/hr, respectively, with 85% of the drug delivered in 7.0 hours. The dosage form can be kept in the oral cavity until the osmotic layer reaches the delivery orifice, or kept in the oral cavity for 3-4 hours before swallowed.

In a specific preferred embodiment, the pharmaceutical composition is composed of a drug pull-layer, an osmotic push-layer and a coating membrane, wherein the drug pull-layer is composed of 40% weight percentage of levodopa, 10.8% weight percentage of carbidopa, 31% weight percentage of hydroxypropyl cellulose, 12.7% weight percentage of mannitol, 5% weight percentage of citric acid and 0.5% weight percentage of Povidone K30, wherein the weight percentage is its weight percentage of the drug pull-layer; the osmotic push-layer is composed of 55% weight percentage of sodium carboxymethyl cellulose 7H4XF, 5% weight percentage of Povidone K30, 39% weight percentage of sorbitol, 0.5% weight percentage of iron oxide red and 0.5% weight percentage of magnesium stearate, wherein the weight percentage is its weight percentage of the osmotic push-layer; the coating membrane is composed of 60% weight percentage of cellulose acetate membrane and 40% weight percentage of Copovidone VA64, wherein the weight percentage is its weight percentage of the coating membrane; and the weight of the coating membrane is 5.0% of the weight of the tablet core; the dosage form comprising the pharmaceutical composition delivers 85% of the drug in 6 hours. The dosage form can be kept in the oral cavity until the osmotic layer reaches the delivery orifice, or kept there for 2-3 hours before swallowed.

In a specific preferred embodiment, the pharmaceutical composition is composed of a drug pull-layer, an osmotic push-layer and a coating membrane, wherein the drug pull-layer is composed of 45% weight percentage of levodopa, 31% weight percentage of hydroxypropyl cellulose, 16% weight percentage of mannitol, 5% weight percentage of Povidone K30, 1% weight percentage of magnesium stearate, 1% weight percentage of Mint flavor and 1% weight percentage of aspartame, wherein the weight percentage is its weight percentage of the drug pull-layer; the osmotic push-layer is composed of 55% weight percentage of sodium carboxymethyl cellulose 7H4XF, 10% weight percentage of Povidone K30, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 60% weight percentage of cellulose acetate membrane and 40% weight percentage of Copovidone VA64, wherein the weight percentage is its weight percentage of the coating membrane; and the weight of the coating membrane is 4.2%, 6.7% or 9.7% of the weight of the tablet core. The dosage forms comprising the pharmaceutical composition having membrane weight gains of 4.2%, 6.7%, and 9.7%, deliver levodopa at an average rate of 38.3 mg/hr, 27.3 mg/hr, and 21.3 mg/hr, respectively, correspondingly with 85% of levodopa delivered in 5.0, 7.0 and 9.0 hours, respectively.

In a specific preferred embodiment, the pharmaceutical composition is composed of a drug pull-layer, an osmotic push-layer and a coating membrane, wherein the drug pull-layer is composed of 45% weight percentage of levodopa, 31% weight percentage of hydroxymethyl cellulose, 16% weight percentage of mannitol, 5% weight percentage of Povidone K30, 1% weight percentage of magnesium stearate, 1% weight percentage of Mint flavor and 1% weight percentage of aspartame, wherein the weight percentage is its weight percentage of the drug pull-layer; the osmotic push-layer is composed of 55% weight percentage of sodium carboxymethyl cellulose 7H4XF, 10% weight percentage of Povidone K30, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% weight percentage of cellulose acetate membrane and 30% weight percentage of Copovidone VA64, wherein the weight percentage is its weight percentage of the coating membrane; and the weight of the coating membrane is 4.6% or 7.9% of the weight of the tablet core. The dosage form comprising the pharmaceutical composition having membrane weight gains of 4.6% and 7.9%, deliver levodopa at an average rate of 25.5 mg/hr and 16.9 mg/hr, respectively, and correspondingly with 85% of levodopa delivered in 7.5 hours and 11.5 hours, respectively.

In a specific preferred embodiment, the pharmaceutical composition is composed of a drug pull-layer, an osmotic push-layer and a coating membrane, wherein the drug pull-layer is composed of 70% weight percentage of levodopa, 9% weight percentage of mannitol, 20% weight percentage of Povidone K30 and 1% weight percentage of magnesium stearate, wherein the weight percentage is its weight percentage of the drug pull-layer; the osmotic push-layer is composed of 85% weight percentage of sodium carboxymethyl cellulose, 3% weight percentage of Povidone K30, 5% weight percentage of sorbitol, 5% weight percentage of iron oxide red and 2% weight percentage of magnesium stearate, wherein the weight percentage is its weight percentage of the osmotic push-layer; the coating membrane is composed of 70% weight percentage of cellulose acetate membrane and 30% weight percentage of Copovidone VA64, wherein the weight percentage is its weight percentage of the coating membrane; and the weight of the coating membrane is 4.5% of the weight of the tablet core. The dosage form containing the pharmaceutical composition delivers levodopa at an average rate of 35.0 mg/hr with 85% of levodopa delivered in 8.5 hours.

In a specific preferred embodiment, the pharmaceutical composition is composed of a drug pull-layer, an osmotic push-layer and a coating membrane, wherein the drug pull-layer is composed of 20% weight percentage of levodopa, 20% weight percentage of carbidopa, 50% weight percentage of hydroxypropyl cellulose, 4% weight percentage of mannitol, 5% weight percentage of aspartame and 1% weight percentage of magnesium stearate, wherein the weight percentage is its weight percentage of the drug pull-layer; the osmotic push-layer is composed of 25% weight percentage of sodium carboxymethyl cellulose, 9.5% weight percentage of Povidone K30, 65% weight percentage of sorbitol and 0.5% weight percentage of magnesium stearate, wherein the weight percentage is its weight percentage of the osmotic push-layer; the coating membrane is composed of 90% weight percentage of cellulose acetate membrane and 10% weight percentage of Copovidone VA64, wherein the weight percentage is its weight percentage of the coating membrane; and the weight of the coating membrane is 4.5% of the weight of the tablet core. The dosage form comprising the pharmaceutical composition delivers levodopa and carbidopa at an average rate of 7.1 mg/hr, with 85% of levodopa/carbidopa delivered in 12 hours.

In a specific preferred embodiment, the pharmaceutical composition is composed of a drug pull-layer, an osmotic push-layer, a coating membrane and an overcoat, wherein the drug pull-layer is composed of 45% weight percentage of levodopa, 31% weight percentage of hydroxypropyl cellulose, 16% weight percentage of mannitol, 5% weight percentage of Povidone K30, 1% weight percentage of magnesium stearate, 1% weight percentage of Mint flavor and 1% weight percentage of aspartame, wherein the weight percentage is its weight percentage of the drug pull-layer; the osmotic push-layer is composed of 55% weight percentage of sodium carboxymethyl cellulose 7H4XF, 10% weight percentage of Povidone K30, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% weight percentage of cellulose acetate membrane and 30% weight percentage of Copovidone VA64, wherein the weight percentage is its weight percentage of the coating membrane, and the weight of the coating membrane is 4.8% or 7.7% of the weight of the tablet core; the overcoat comprises an immediate-release composition comprising 23.78% weight percentage of levodopa, 64.22% weight percentage of carbidopa, 10% weight percentage of hydroxypropyl cellulose, 1% weight percentage of aspartame and 1% weight percentage of Mint flavor, wherein the weight percentage is its weight percentage of the overcoat, and the overcoat weight gains relative to the tablet core are 13.2% and 12.9%, respectively. The release profile of the dosage form comprising the pharmaceutical composition shows rapid release of levodopa/carbidopa, and the subsequent release durations of extended release of the dosage forms with coating membrane weight gains of 4.8% and 7.7% are approximately 8.5 hours and 12.0 hours, respectively. Dosage forms having a membrane weight gain of 4.8% can be kept in the oral cavity for 4-5 hours, and then kept in the oral cavity at meal time or the whole release duration. Dosage forms having a membrane weight gain of 7.7% can be kept in the oral cavity for 8-9 hours before swallowed, or kept in the oral cavity for the whole release duration.

In a specific preferred embodiment, the pharmaceutical composition is composed of a drug pull-layer, an osmotic push-layer, a coating membrane and an overcoat, wherein the drug pull-layer is composed of 45% weight percentage of levodopa, 31% weight percentage of hydroxypropyl cellulose, 17% weight percentage of mannitol, 5% weight percentage of Povidone K30, 1% weight percentage of magnesium stearate and 1% weight percentage of aspartame, wherein the weight percentage is its weight percentage of the drug pull-layer; the osmotic push-layer is composed of 60% weight percentage of sodium carboxymethyl cellulose 7H4XF, 10% weight percentage of Povidone K30, 26% weight percentage of sorbitol, 2% weight percentage of iron oxide red and 2% weight percentage of magnesium stearate, wherein the weight percentage is its weight percentage of the osmotic push-layer; the coating membrane is composed of 70% weight percentage of cellulose acetate membrane and 30% weight percentage of Copovidone VA64, wherein the weight percentage is its weight percentage of the coating membrane, and the weight of the coating membrane is 4.8% of the weight of the tablet core; the overcoat comprises an immediate-release composition comprising 93% weight percentage of carbidopa, 2% weight percentage of hydroxypropyl cellulose and 5% weight percentage of aspartame, wherein the weight percentage is its weight percentage of the overcoat, and the weight gain of the overcoat relative to the tablet core is 13.2% weight percentage. The immediate-release overcoat of the dosage form is first released rapidly, followed by an extended release with a release duration of approximately 8 hours. The dosage form can be kept in the oral cavity for 4-5 hours, and then was swallowed before meal time or kept in the oral cavity for the whole release duration.

In a specific preferred embodiment, the pharmaceutical composition is composed of a drug pull-layer, an osmotic push-layer, a coating membrane and an overcoat, wherein the drug pull-layer is composed of 45% weight percentage of levodopa, 31% weight percentage of hydroxypropyl cellulose, 12% weight percentage of mannitol, 5% weight percentage of Povidone K30, 5% weight percentage of Mint flavor, 1% weight percentage of aspartame and 1% weight percentage of magnesium stearate, wherein the weight percentage is its weight percentage of the drug pull-layer; the osmotic push-layer is composed of 40% weight percentage of sodium carboxymethyl cellulose 7H4XF, 20% weight percentage of Povidone K30, 36% weight percentage of sorbitol, 3.5% weight percentage of iron oxide red and 0.5% weight percentage of magnesium stearate, wherein the weight percentage is its weight percentage of the osmotic push-layer; the coating membrane is composed of 70% weight percentage of cellulose acetate membrane and 30% weight percentage of Copovidone VA64, wherein the weight percentage is its weight percentage of the coating membrane, and the weight of the coating membrane is 4.8% of the weight of the tablet core; the overcoat comprises an immediate-release composition comprising 75% weight percentage of levodopa, 20% weight percentage of hydroxypropyl cellulose and 5% weight percentage of Mint flavor, wherein the weight percentage is its weight percentage of the overcoat. The overcoat weight gain relative to the tablet core is 13.2% weight percentage. The immediate-release overcoat of the dosage form is first released rapidly, followed by an extended release with a release duration of approximately 8 hours. The dosage form can be kept in the oral cavity for 4-5 hours, and then was swallowed before meal time or kept in the oral cavity for the whole release duration.

In a specific preferred embodiment, the pharmaceutical composition is composed of a drug pull-layer, an osmotic push-layer, a coating membrane and an overcoat, wherein the drug pull-layer is composed of 45% weight percentage of levodopa, 31% weight percentage of hydroxymethyl cellulose, 16% weight percentage of mannitol, 5% weight percentage of Povidone K30, 1% weight percentage of magnesium stearate, 1% weight percentage of Mint flavor and 1% weight percentage of aspartame, wherein the weight percentage is its weight percentage of the drug pull-layer; the osmotic push-layer is composed of 55% weight percentage of sodium carboxymethyl cellulose 7H4XF, 10% weight percentage of hydroxypropyl cellulose, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% weight percentage of cellulose acetate membrane and 30% weight percentage of Copovidone VA64, wherein the weight percentage is its weight percentage of the coating membrane, wherein the cellulose acetate comprises 39.8 Wt % of acetyl acetate membrane, and the weight of the coating membrane is 5.9% of the weight of the tablet core; and, the overcoat is composed of 64.22% weight percentage of levodopa, 23.78% weight percentage of carbidopa, 10% weight percentage of hydroxypropyl cellulose, 1% weight percentage of aspartame and 1% weight percentage of Mint flavor, wherein the weight percentage is its weight percentage of the overcoat, and the weight of the overcoat is 13.1% of the total weight of the membrane-coated tablet. When the solvent of the overcoat suspension is anhydrous ethanol, the content of the carbidopa-related genotoxic impurity hydrazine in the obtained dosage form is 1.7 ppm, and the content of the carbidopa-related impurity dihydroxyphenylacetone (DHPA) is 0.21%. When the solvent of the overcoat suspension is purified water, the concentration of the solid suspension of the overcoat is 10.0 Wt %, comprising, in weight percentage, 24.0 Wt % of levodopa, 65.0 Wt % of carbidopa monohydrate, 10.0 Wt % of hydroxypropyl cellulose and 1.0 Wt % of aspartame; the content of the carbidopa-related genotoxic impurity hydrazine in the obtained dosage form is 3.8 ppm, and the content of the carbidopa-related impurity DHPA is 0.28%. The carbidopa-related genotoxic impurity hydrazine and impurity DHPA of the obtained dosage form when the solvent of the coating liquid of the overcoat is anhydrous ethanol, are significantly lower than those of the obtained dosage form when the solvent of the coating liquid is purified water. The immediate-release overcoat of the dosage form is first released rapidly, followed by an extended release with a release duration of approximately 8 hours. The dosage form can be kept in the oral cavity for 3-5 hours, and then was swallowed before meal time or kept in the oral cavity for the whole release duration.

In a specific preferred embodiment, the pharmaceutical composition is composed of a drug pull-layer, an osmotic push-layer, a coating membrane and an overcoat; wherein the drug pull-layer is composed of 45% weight percentage of levodopa, 31% weight percentage of hydroxypropyl cellulose, 22% weight percentage of mannitol, 0.9% weight percentage of aspartame, 0.5% weight percentage of magnesium stearate and 0.1% weight percentage of Mint flavor, wherein the weight percentage is its weight percentage of the drug pull-layer; the osmotic push-layer is composed of 55% weight percentage of sodium carboxymethyl cellulose 7H4XF, 10% weight percentage of hydroxypropyl cellulose, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% of cellulose acetate and 30% of Copovidone V64, wherein the weight percentage is its weight percentage of the coating membrane; wherein the cellulose acetate comprises 39.8 Wt % of acetyl acetate membrane, and the weight of the coating membrane is 6.5% of the weight of the tablet core; and, the overcoat is composed of 54% weight percentage of levodopa, 35% weight percentage of carbidopa, 10% weight percentage of hydroxypropyl cellulose and 0.9% weight percentage of aspartame and 0.1% weight percentage of Mint flavor, wherein the weight percentage is its weight percentage of the overcoat. The final dosage form comprises an immediate-release coating comprising 62.5 mg of levodopa and 37.5 mg of carbidopa, and 187.5 mg of levodopa is comprised in a controlled-release drug layer. The immediate-release overcoat of the dosage form is first released rapidly, followed by an extended release with a release duration of approximately 8 hours.

The osmotic delivery system can be kept in the oral cavity for 4-5 hours, and then was swallowed before meal time or kept in the oral cavity for the whole release duration.

In a specific preferred embodiment, the pharmaceutical composition is composed of a drug pull-layer, an osmotic push-layer, a coating membrane and an overcoat; wherein the drug pull-layer is composed of 45% weight percentage of levodopa, 31% weight percentage of hydroxypropyl cellulose, 22% weight percentage of mannitol, 0.9% weight percentage of aspartame, 0.5% weight percentage of magnesium stearate and 0.1% weight percentage of Mint flavor, wherein the weight percentage is its weight percentage of the drug pull-layer: the osmotic push-layer is composed of 55% weight percentage of sodium carboxymethyl cellulose 7H4XF, 10% weight percentage of hydroxypropyl cellulose, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% of cellulose acetate and 30% of Copovidone V64, wherein the weight percentage is its weight percentage of the coating membrane; wherein the cellulose acetate comprises 39.8 Wt % of acetyl acetate membrane, and the weight of the coating membrane is 7.0% of the weight of the tablet core; and, the overcoat is composed of 42.8% weight percentage of levodopa, 46.2% weight percentage of carbidopa, 10% weight percentage of hydroxypropyl cellulose and 0.9% weight percentage of aspartame and 0.1% weight percentage of Mint flavor, wherein the weight percentage is its weight percentage of the overcoat. The final dosage form comprises an immediate-release coating comprising 37.5 mg of levodopa and 37.5 mg of carbidopa, and a controlled-release drug layer comprising 112.5 mg of levodopa. The immediate-release overcoat of the dosage form is first released rapidly, followed by an extended release with a release duration of approximately 8 hours. The osmotic delivery system can be kept in the oral cavity for 4-5 hours, and then was swallowed before meal time or kept in the oral cavity for the whole release duration.

In a specific preferred embodiment, the pharmaceutical composition is composed of a drug pull-layer, an osmotic push-layer, a coating membrane and an overcoat; wherein the drug pull-layer is composed of 45% weight percentage of levodopa, 31% weight percentage of hydroxypropyl cellulose, 22% weight percentage of mannitol, 0.9% weight percentage of aspartame, 1% weight percentage of magnesium stearate and 0.1% weight percentage of Mint flavor, wherein the weight percentage is its weight percentage of the drug pull-layer: the osmotic push-layer is composed of 55% weight percentage of sodium carboxymethyl cellulose 7H4XF, 10% weight percentage of hydroxypropyl cellulose, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% of cellulose acetate and 30% of Copovidone V64, wherein the weight percentage is its weight percentage of the coating membrane: wherein the cellulose acetate comprises 39.8 Wt % of acetyl acetate membrane, and the weight of the coating membrane is 9.0% of the weight of the tablet core; and, the overcoat is composed of 28.2% weight percentage of levodopa, 60.8% weight percentage of carbidopa, 10% weight percentage of hydroxypropyl cellulose and 0.9% weight percentage of aspartame and 0.1% weight percentage of Mint flavor, wherein the weight percentage is its weight percentage of the overcoat. The final dosage form comprises an immediate-release coating comprising 18.75 mg of levodopa and 37.5 mg of carbidopa, and 56.25 mg of levodopa is comprised in a controlled-release drug layer. The immediate-release overcoat of the dosage form is first released rapidly, followed by an extended release with a release duration of approximately 8 hours. The osmotic delivery system can be kept in the oral cavity for 4-5 hours, and then was swallowed before meal time or kept in the oral cavity for the whole release duration.

A method for preparing the above-mentioned overcoat comprising dissolving the above-mentioned weight percentage of each component of the overcoat in anhydrous ethanol to prepare a coating suspension, and the ratio of all components of the overcoat to anhydrous ethanol is preferably 1:10. In the pharmaceutical composition, carbidopa only exists in an immediate-release coating, and the tablet core of the sustained release tablet does not comprise carbidopa. The dosage form has the following advantages: the content of carbidopa-related genotoxic impurity hydrazine and the impurity dihydroxyphenylacetone (DHPA) is lower. When the solvent for the coating suspension of the overcoat is anhydrous ethanol, carbidopa-related genotoxic impurity hydrazine and impurity DHPA of the obtained dosage form are significantly lower than those of the obtained dosage form when the solvent for the coating suspension is purified water.

Unless otherwise specified, the method for preparing the aforementioned pharmaceutical composition is a conventional preparation method in the art.

Preferably, as mentioned above, the pharmaceutical composition is an osmotic pump controlled-release drug delivery system (also referred to as an osmotic delivery system in a specific embodiment of the present invention); preferably, the osmotic pump controlled-release drug delivery system is a controlled-release tablet; more preferably, the controlled-release tablet has a cylindrical shape with a diameter of 5-10 mm and a height of 5-30 mm, or a capsule shape with a length of 10-25 mm and a width of 5-10 mm.

The osmotic pump controlled-release drug delivery system is an upper gastrointestinal tract (UGI) osmotic pump controlled-release drug delivery system. Firstly, the above-mentioned oral osmotic pump controlled-release drug delivery system is kept in the oral cavity, after swallowing, the pharmaceutical ingredients in the oral osmotic pump controlled-release drug delivery system is absorbed in the gastrointestinal tract. Preferably, the oral osmotic pump controlled-release drug delivery system has a retention duration in the oral cavity of 1-17 hours, and the gastrointestinal tract absorbs 85% of active pharmaceutical ingredients of the pharmaceutical composition for 4 to 20 hours; more preferably, the retention duration in the oral cavity is 2-9 hours, and the gastrointestinal tract absorbs 85% of the active pharmaceutical ingredients of the pharmaceutical composition for 6 to 12 hours.

The osmotic pump controlled-release drug delivery system may be an osmotic pump controlled-release drug delivery system comprising but not limited to LD and CD. The osmotic pump controlled-release drug delivery system may be a single-layer elementary osmotic pump, a bi-layer push-pull system, or a bi-layer push-pull osmotic pump controlled-release drug delivery system with an immediate-release overcoat. The osmotic pump controlled-release drug delivery system provides consistent and constant release of LD/CD in the oral cavity, in stark contrast to a matrix extended release system that is sensitive to oral conditions such as pH, the presence or absence of saliva, and intentional or unintentional grinding with the tongue of hydrated matrix tablets.

The osmotic pump controlled-release drug delivery system of the present invention can also become an osmotic pump controlled-release system if the APIs are removed, and can also become a controlled-release delivery platform, in which other APIs can be incorporated later for the treatment of other diseases.

In order to solve the above technical problems, in one aspect of the technical solutions, the present invention provides a method for preparing the above-mentioned pharmaceutical composition or UGI osmotic pump controlled-release drug delivery system, which adopts the following methods: method 1, method 2 or method 3;

method 1 includes the following steps: coating the tablet core comprising the drug pull-layer with an outer coating membrane;

method 2 includes the following steps: coating the tablet core comprising the drug pull-layer and the osmotic push-layer with a coating membrane;

or method 3 includes the following steps: coating the tablet core comprising the drug pull-layer and the osmotic push-layer with a coating membrane; and then overcoating the membrane-coated tablet with an overcoat.

In a specific embodiment, in the method 1, the method 2 and the method 3, the preparation of the tablet core includes the following steps:

(11) using wet or dry granulation to obtain the drug pull-layer granules: the weight of the drug pull-layer is 125-500 mg, preferably 125 mg, 250 mg, 418 mg, or 500 mg;

The preparation of the coating membrane includes the following steps:

(21) dissolving the cellulose acetate and Copovidone in acetone according to the weight percentage thereof; preferably preparing a 4% of solid solution;

(22) coating the tablet core with the solid solution obtained in the above step to form a coating membrane; the coating is preferably spray coating;

(23) drilling orifices through the coating membrane.

In a specific preferred embodiment, in the method 2 and the method 3, the preparation of the tablet core further includes the following steps:

(12) granulating to form osmotic push-layer granules: the weight of the osmotic push-layer is 62.5-250 mg, preferably 62.5 mg, 125 mg, 209 mg, or 250 mg;

(13) compressing the drug pull-layer granules and the osmotic push-layer granules into a bi-layer tablet core; preferably, the weight ratio of the drug pull-layer granules and the osmotic push-layer granules is 2:1;

In a specific more preferred embodiment, in the method 3, the preparation of the overcoat includes the following steps:

(31) dissolving the components of the overcoat in an alcohol solvent according to the weight percentage thereof to prepare a coating suspension; preferably, the ratio of all the components of the overcoat and the alcohol solvent is 1:10; and the alcohol solvent is preferably one or more of methanol, ethanol, ethylene glycol, propylene glycol, isopropanol and n-butanol, more preferably anhydrous ethanol;

(32) coating the above membrane-coated tablet with the coating suspension obtained in the above step, the coating is preferably a spray coating. One of the UGI osmotic pump controlled-release drug delivery systems of the present invention is a single-layer elementary osmotic pump, which can be manufactured by standard manufacturing technology. First, the tablet core granulation can be prepared by the conventional wet granulation method using a high-shear granulator or a fluid-bed granulator. Second, the granulation is pressed into a single-layer tablet core with a tablet press. Next, the tablet core is coated with a coating composition of the semi-permeable membrane. Finally, a passageway is drilled through the coating membrane.

Another UGI osmotic pump controlled-release drug delivery system in the present invention is a bi-layer push-pull osmotic pump, which can be manufactured as follows. First, a high-shear granulator or a fluid-bed granulator can be used to prepare a drug layer granule and an osmotic layer granule. Second, the granules of these two layers are pressed into a bi-layer tablet core in a tablet press. Next, the bi-layer tablet core is coated with a coating composition of the semi-permeable membrane. Finally, an orifice is drilled through the coating membrane on the side of drug pull-layer.

Another UGI osmotic pump controlled-release drug delivery system in the present invention is a bi-layer push-pull osmotic pump with an immediate-release overcoat, and can be manufactured as follows. First, a high-shear granulator or a fluid-bed granulator can be used to prepare a drug layer granule and an osmotic layer granule. Second, the granules of these two layers are pressed into a bi-layer tablet core in a tablet press. Next, the bi-layer tablet core is coated with a coating composition of the semi-permeable membrane. Then an orifice is drilled through the coating membrane on the side of the drug layer. Finally, the drilled tablet core is overcoated with an immediate-release coating composition of LD/CD.

The semi-permeable membrane of the permeable dosage form can be formed using air suspension technology. The process involves suspending and tumbling the single-layer or bi-layer tablet cores in an air current and a coating composition until the membrane is formed homogeneously around the cores. The air suspension step can be achieved using a fluid-bed granulator with a Wurster® insert. Acetone or acetone-ethanol mixed cosolvent with or without a minor amount of deionized water can be used as a coating solvent, in which 2.0-5 Wt % of membrane-forming compositions can be dissolved. Other membrane-forming techniques such as pan coating can also be used. In the pan coating system, a membrane-forming composition is deposited by continuous spraying of the composition on the tablet core while tumbling in a rotating pan. Generally, the membranes formed by these techniques have a thickness of 25-250 µm, preferably 100-150 µm.

The LD/CD immediate-release overcoat can be formed by using a pan coater. In a pan coater, the drug suspension with a membrane-forming polymer is deposited by continuous spraying of the suspension on the tablet cores while tumbling in a rotating pan. The overcoat formed by using the pan coater usually comprises 10-75 mg of CD and 10-100 mg of LD.

In order to solve the above technical problems, in one aspect of the technical solutions, the present invention provides a pharmaceutical composition or an osmotic pump controlled-release drug delivery system prepared according to the aforementioned methods.

On the basis of conforming to common knowledge in the art, the above-mentioned preferred conditions can be arbitrarily combined to obtain each preferred embodiment of the present invention.

The reagents and raw materials used in the present invention are all commercially available.

Advantageous effects of the present invention are that the present invention provides an osmotic pump controlled-release drug delivery system capable of improving the bioavailability of a pharmaceutical composition with an absorption window, to provide non-invasive controlled-release products with a stable plasma profile of active pharmaceutical ingredient such as levodopa, or levodopa and carbidopa.

DETAILED DESCRIPTION OF THE ILLUSTRATED EMBODIMENTS

Before further describing the invention, it should be understood that the invention is not limited to the particular embodiments described below. The active pharmaceutical ingredients (APIs) used in the present invention include, but are not limited to, Levodopa (LD)/Carbidopa (CD), baclofen, acyclovir, valacyclovir, ganciclovir, metformin and gabapentin.

Figure 1:
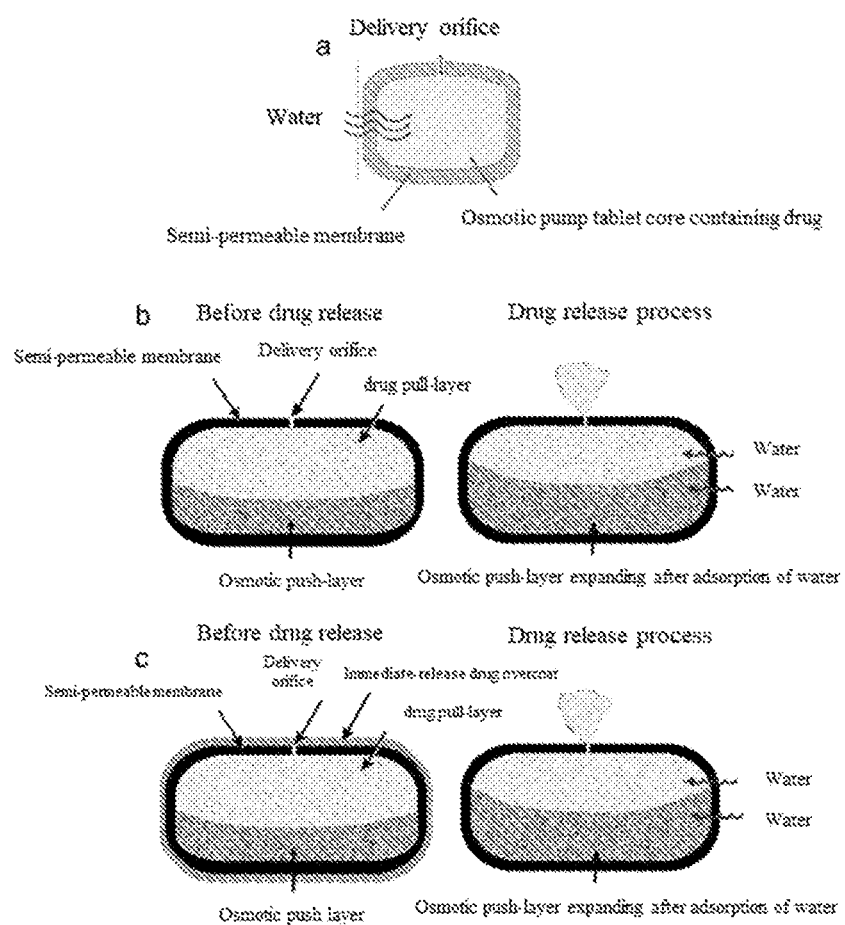
FIG. 1 is a schematic diagram of the osmotic pump controlled-release drug delivery system of the upper gastrointestinal tract: a. Single-layer elementary osmotic pump (EOP), b. Bi-layer osmotic push-pull system, c. Bi-layer osmotic push-pull system with drug overcoat.

In one embodiment, the API is LD/CD that is incorporated into a single-layer elementary osmotic pump (EOP) known in the art (U.S. Pat. Nos. 3,845,770 and 3,916,899). As shown in FIG. 1.a, EOP is composed of a tablet core containing the API and a rate-controlling membrane, that is the coating membrane, enclosing the tablet core. EOP comprises at least one orifice through the membrane so that LD/CD can be released into oral cavity through the orifice. The tablet core contains LD/CD, an osmotic agent, microcrystalline cellulose (MCC), a binding agent, a lubricant, a flavoring agent (optional), an acidifying agent (optional) and an antioxidant (optional). The flux enhancer of the present invention includes, but is not limited to, polyethylene glycol, Povidone, Copovidone, and other water-soluble polymers. The preferred flux enhancer is Copovidone (VA64), which is soluble in both water and organic solvents such as acetone, methanol, ethanol and isopropanol. The use of the Copovidone dissolved in acetone or a mixed solvent of acetone/ethanol can easily produce a more homogeneous membrane, resulting in a more consistent release profile than others.

In another embodiment, LD/CD or LD only is incorporated into the bi-layer push-pull osmotic delivery systems known in the art (U.S. Pat. Nos. 4,327,725, 4,612,008, 5,200,195 and 5,869,096). As shown in FIG. 1.b, the push-pull osmotic delivery system comprises a bi-layer core containing a drug pull-layer (referred to as a drug layer) and an osmotic push-layer (referred to as an osmotic layer) and a rate-controlling membrane enclosing the core. The push-pull osmotic delivery system includes at least one orifice through the side of the membrane comprising the drug pull-layer, so that the contents of the pulling layer can be released to oral cavity through the orifice.

The drug layer comprises LD/CD, a hydrophilic polymer, an osmotic agent, a binding agent, a lubricant, a flavoring agent (optional), an acidifying agent (optional), an antioxidant (optional). The osmotic push-layer comprises a high molecular weight hydrophilic polymer, an osmotic agent, a binding agent, a lubricant and a colorant (optional).

The osmotic pump controlled-release drug delivery system operates by imbibing water or moisture through the rate-controlling membrane into a bi-layer core to hydrate the both layers, thereby causing the osmotic push-layer to expand and push the hydrated dispensable drug pull-layer preparation from the system through the orifice.

Due to the presence of the hydrophilic polymer, the push-layer composition can retain a large amount of water within the layer. The hydrophilic polymer can be κ-carrageenan, sodium carboxymethyl cellulose, and polyethylene oxide having a molecular weight of 75,000-7,500,000.

The osmotic agent used in the present invention is selected from the group consisting of magnesium sulfate, magnesium chloride, sodium chloride, lithium chloride, potassium sulfate, sodium sulfate, mannitol, urea, sorbitol, inositol, sucrose, glucose and the like. Mannitol and sorbitol are the preferred osmotic agents because of the release of the drug layer formulation in oral cavity and thus concerns for taste and cariogenicity.

In another embodiment of the present invention, the bi-layer push-pull membrane coated tablet can be overcoated with an immediate-release LD/CD preparation, thereby providing an initial rapid release of LD/CD, followed by an extended release of LD/CD or LD only.

Figure 2:
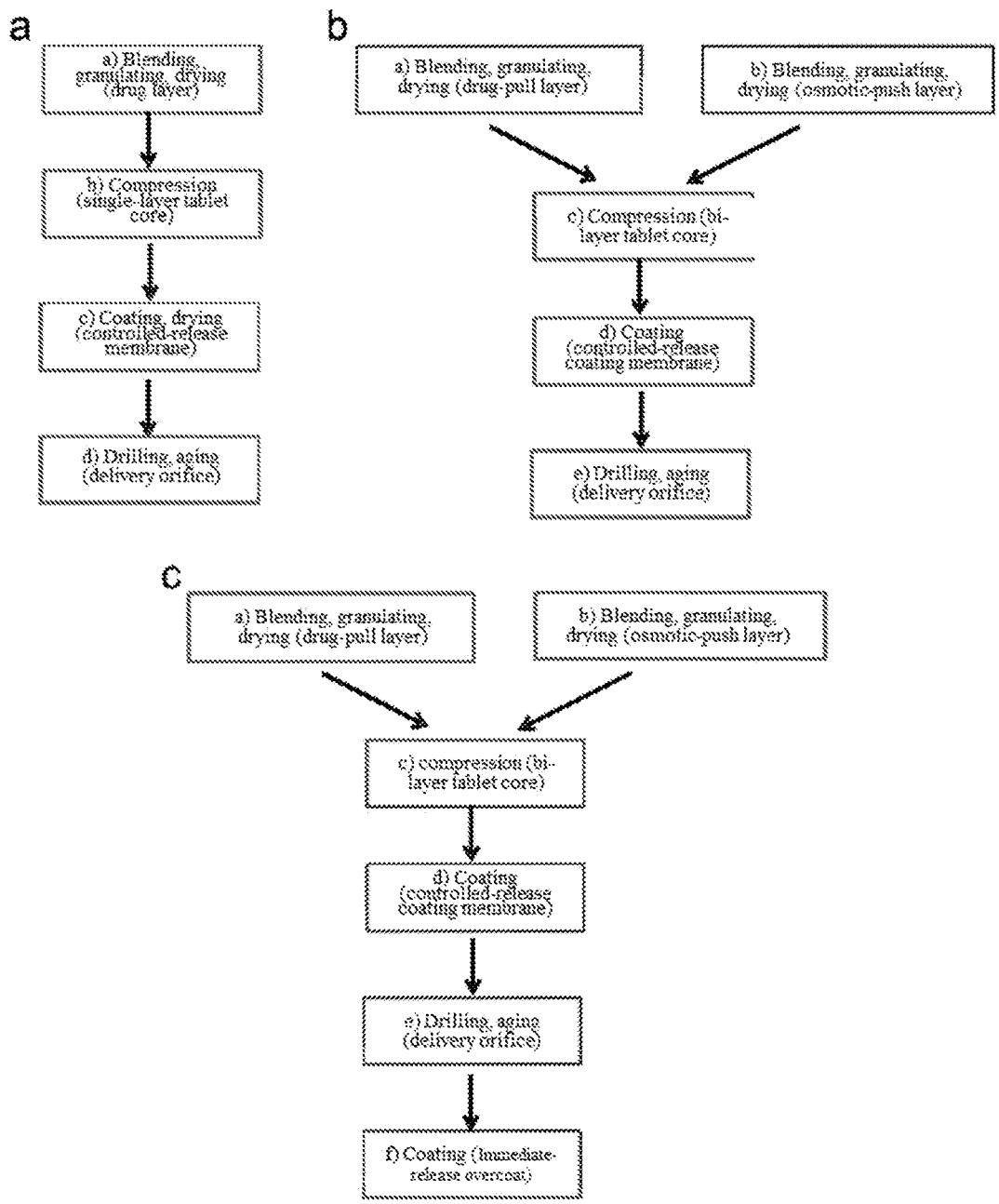
FIG. 2 is a flowchart of osmotic pump controlled-release drug delivery system manufactured by the present invention: a. Single-layer elementary osmotic pump (EOP), b. Bi-layer osmotic push-pull system, c. Bi-layer osmotic push-pull system with drug overcoat.

A flowchart for manufacturing an UGI controlled-release system is shown in FIG. 2. FIG. 2.a shows a single-layer elementary osmotic pump (EOP), FIG. 2.b shows a bi-layer osmotic push-pull system, and FIG. 2.c shows a bi-layer osmotic push-pull system with drug overcoat.

In another embodiment of the present invention, an administration of the osmotic pump controlled-release drug delivery system, either the single-layer EOP or the bi-layer push-pull system or the bi-layer osmotic push-pull system with an immediate-release overcoat, can be designed to achieve prolonged retention time of the gastrointestinal delivery system, for example, not less than 4 hours. In this mode of administration, the osmotic delivery system is kept in oral cavity for 3-4 hours less than the release duration before swallowing at meal time or the whole release duration, where the release duration is defined as the time when 85% of the labeled amount of API(s) released.

The present invention is further described below by means of embodiments, but the present invention is not therefore limited to the scope described by embodiments. In the following embodiments, experimental methods without certain conditions specified shall be selected in accordance with conventional methods and conditions, or according to the instruction of commodity.

EXAMPLE 1

A dosage form for dispensing the beneficial drugs levodopa and carbidopa to oral cavity was manufactured as follows: first, a tablet core was prepared, comprising, in weight percentage, 40.0 Wt % of levodopa (LD), 10.8 Wt % of carbidopa monohydrate (CD), 20.0 Wt % of microcrystalline cellulose, 18.7 Wt % of mannitol, 5.0 Wt % of hydroxypropyl methylcellulose (HPMC E5) and 5.0 Wt % of citric acid that were each passed through a 40-mesh stainless steel sieve, then blended and granulated with pure water until homogeneous wet mass was formed; the wet mass was passed through a 20-mesh stainless steel sieve and dried at 80° C. for 2 hours; the dried granules were passed through an 18-mesh stainless steel sieve and then mixed with 0.5 Wt % of magnesium stearate.

Next, 500 mg of the drug core granules were compressed into a single-layer tablet core with a 9.0 mm round punch using a tablet press.

Figure 3:
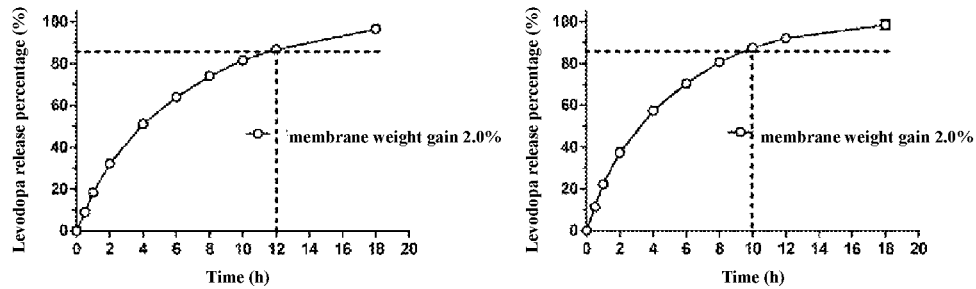
FIG. 3 shows the release profile of the UGI osmotic pump controlled-release drug delivery system described in Example 1.

Next, the single-layer tablet core was coated with a semi-permeable membrane. The membrane-forming composition comprised, in weight percentage, 50 Wt % of cellulose acetate and 50 Wt % of Copovidone VA64. The membrane-forming composition was dissolved in acetone to make a 4% of solid solution. Using the process parameters listed in the table below, the membrane-forming composition was sprayed onto the tablet cores in a Glatt GC 1 pan coater to form a coating membrane. The membrane weight gain of the coated tablet was 2.0%. Finally, a 0.5 mm exit orifice was drilled mechanically on the drug layer side of the coated tablet. Residual solvents were removed by drying the dosage form at 40° C. and ambient humidity for 24 hours. As shown in FIG. 3, the final manufactured dosage form delivered LD and CD at an average rate of 14.17 mg/hr and 4.59 mg/hr, with 85% of the drugs delivered in 12 and 10 hours, respectively. The osmotic delivery system can be kept in oral cavity until the push-layer reaches the delivery orifice, or kept there for 8-9 hours, and then swallowed.

| The process parameters of coating | |
|---|---|
| Inlet temperature (° C.) | 40 |
| Exhaust temperature (° C.) | 21-24 |
| Air flow rate (m³/h) | 20-25 |
| Fluid deliver rate (g/min) | 15-25 |
| Atomizing air pressure (bar) | 0.6-0.8 |
| Pattern air pressure (bar) | 0.6-0.8 |
| Rotating speed of pan (rpm) | 6-8 |
| Batch size (g) | 400 |

EXAMPLE 2

A dosage form designed, shaped and adapted for dispensing the beneficial drugs levodopa and carbidopa monohydrate to oral cavity was manufactured as follows: first, a drug layer composition was prepared, comprising, in weight percentage, 40.0 Wt % of LD, 10.8 Wt % of CD, 31.0 Wt % of hydroxypropyl cellulose having an average molecular weight of 80,000, 12.7 Wt % of mannitol and 5.0 Wt % of citric acid, these excipients were each pass through a 40-mesh stainless steel sieve, then blended and granulated with 95% ethanol until homogeneous wet mass was formed; the wet mass was passed through a 20-mesh stainless steel sieve and dried at 80° C. for 2 hours; the dried granules were passed through a 18-mesh stainless steel sieve and then mixed with 0.5 Wt % of magnesium stearate.

Next, a second composition, the osmosis layer, was prepared, comprising 55.0 Wt % of sodium carboxymethyl cellulose 7H4XF, 39.0 Wt % of sorbitol, 5.0 Wt % of Povidone K30 and 0.5 Wt % of iron oxide red; these components were each passed through a 40-mesh stainless steel sieve, then blended and granulated with 95% ethanol until homogeneous wet mass was formed; the wet mass was passed through a 20-mesh stainless steel sieve and dried at 80° C. for 2 hours; the dried granules were passed through a 18-mesh stainless steel sieve and then mixed with 0.5 Wt % of magnesium stearate.

Next, the drug layer and the osmotic layer granules were pressed into a bi-layer tablet core. First, 500 mg of drug layer granules were added to a 9 mm round punch of a tablet press and tamped, then 250 mg of osmotic layer granules were added to the punch, and the granules of both layers were pressed with a tablet press into a contacting bi-layer tablet core.

Figure 4:
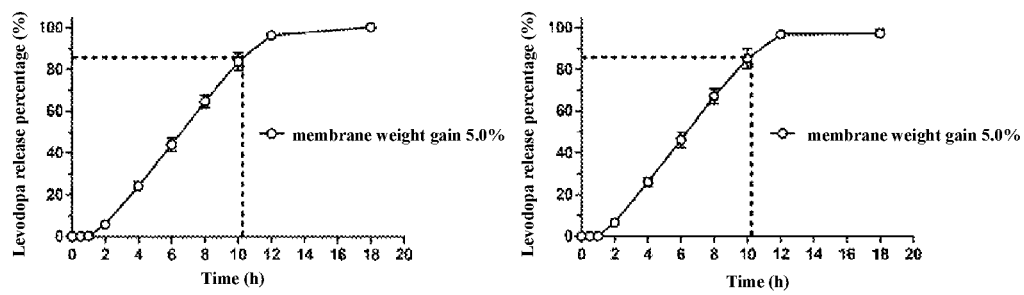
FIG. 4 shows the release profile of the UGI osmotic pump controlled-release drug delivery system described in Example 2.

Next, the bi-layer tablet core was coated with a semi-permeable membrane. The membrane-forming composition comprised, in weight percentage, 70 Wt % of cellulose acetate with an acetyl content of 39.8 Wt %, and 30 Wt % of Copovidone VA64. The membrane-forming composition was dissolved in acetone to make a 4% of solid solution. Using the process parameters listed in Example 1, the membrane-forming composition was sprayed onto the bi-layer tablet core in a Glatt GC 1 pan coater to form a coating membrane, and the membrane weight gain of the coated tablet was 5.0%. Finally, a 0.5 mm exit orifice was drilled mechanically on the drug layer side of the dosage form. Residual solvents were removed by drying the dosage form at 40° C. and ambient humidity for 24 hours. The release profile of the final manufactured dosage form was measured using a USP I paddle method in an aqueous solution of 0.1 N HCl. The final manufactured dosage form delivered LD and CD at an average rate of 17.0 mg/hr and 4.6 mg/hr, respectively, with 85% of LD/CD delivered in 10.0 hours. FIG. 4 depicts the consistent release profiles for both LD and CD. The osmotic delivery system can be kept in oral cavity until the osmotic layer reached the delivery orifice, or kept there for 6-7 hours, and then was swallowed.

EXAMPLE 3

Figure 5:
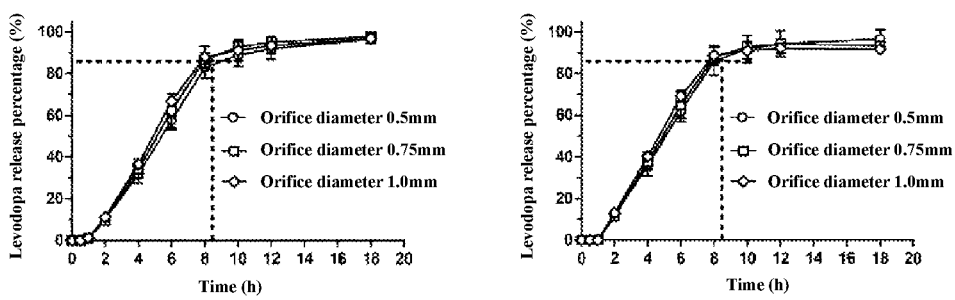
FIG. 5 shows the release profile of the UGI osmotic pump controlled-release drug delivery system described in Example 3.

In this example, the procedures of Example 2 were repeated, and the dosage form consisted of the drug layer, osmotic layer, and coating membrane was identical to those provided in Example 2. In this example, the membrane weight gain was 4.0%, and the size of the delivery orifice varied from 0.5 mm, 0.75 mm, to 1.0 mm. The final manufactured dosage form delivered LD and CD at an average rate of 21.3 mg/hr and 5.7 mg/hr, respectively, with 85% of LD/CD delivered in 8.0 hours. As shown in FIG. 5, the size of the delivery orifice has no significant impact on the release profile. The osmotic delivery system can be kept in oral cavity until the osmotic layer reached the delivery orifice, or kept there for 4-5 hours, and then was swallowed.

EXAMPLE 4

Figure 6:
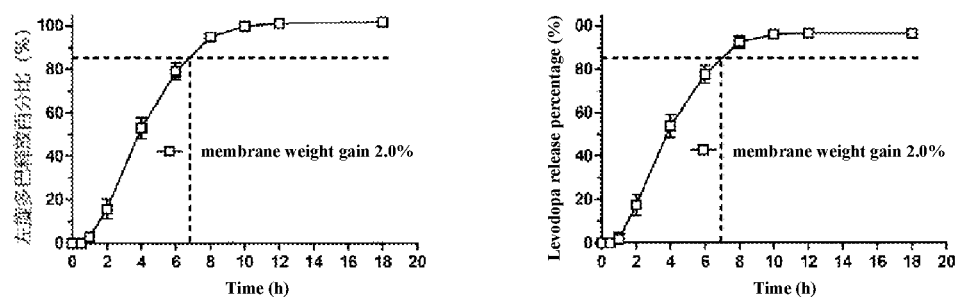
FIG. 6 shows the release profile of the UGI osmotic pump controlled-release drug delivery system described in Example 4.

In this example, the procedures of Example 2 were repeated, and the dosage form consisted of the drug layer was identical to those provided in example 2, while the osmosis layer comprised sodium carboxymethyl cellulose 9H4XF instead of 7H4XF. In this example, the membrane-forming composition and the size of the delivery orifice were also identical to those in Example 1. The coating membrane weight gain of the dosage form was 2.0%. As shown in FIG. 6, the dosage form delivered LD and CD at an average rate of 24.3 mg/hr and 6.6 mg/hr, respectively, with 85% of LD/CD delivered in 7.0 hours. The osmotic delivery system can be kept in oral cavity until the osmotic layer reached the delivery orifice, or kept there for 3-4 hours, and then was swallowed.

EXAMPLE 5

Figure 7:
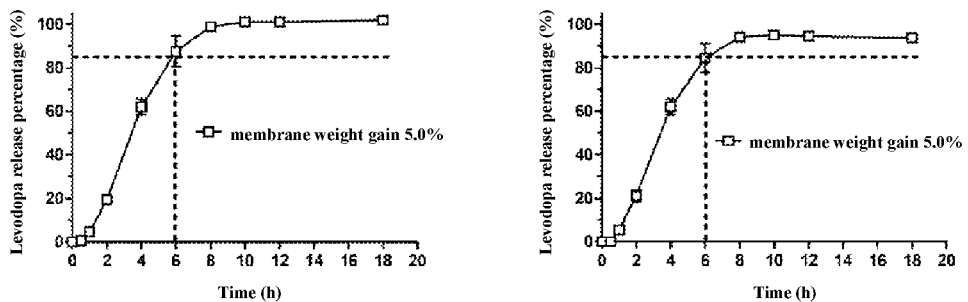
FIG. 7 shows the release profile of the UGI osmotic pump controlled-release drug delivery system described in Example 5.

In this example, the procedures of Example 2 were repeated, and the dosage form consisted of the drug layer and osmotic layer was identical to those provided in Example 2, while the membrane-forming composition comprised 60 wt % of cellulose acetate of cellulose acetate with an acetyl content of 39.8% and 40 Wt % of Copovidone VA64. The membrane weight gain was 5.0%. As shown in FIG. 7, the dosage form delivered 85% of LD/CD in 6 hours. The osmotic delivery system can be kept in oral cavity until the osmotic layer reached the delivery orifice, or kept there for 2-3 hours, and then was swallowed.

EXAMPLE 6

The procedure of Example 2 was repeated in this example for providing a dosage form.

In this embodiment, the drug layer comprised 45.0 Wt % of LD, 31.0 Wt % of hydroxypropyl cellulose (Klucel EXF), 16.0 Wt % of mannitol, 5.0 Wt % of Povidone K30, 1.0 Wt % of aspartame, 1.0 Wt % of Mint flavor and 1.0 Wt % of magnesium stearate. The osmosis layer comprised 55 Wt % of sodium carboxymethyl cellulose 7H4XF, 34.0 Wt % of sorbitol, 10.0 Wt % of Povidone K30 and 0.5 Wt % of iron oxide red and 0.5 Wt % of magnesium stearate.

The drug layer (500 mg) and osmotic layer granules (250 mg) were compressed into a bi-layer tablet core using a 16×7 capsule-shape tooling.

The bi-layer tablet core was coated with the semi-permeable membrane, at three weight gains, 4.2 Wt %, 6.7% and 9.7%, respectively. The membrane-forming composition comprised 60 wt % of cellulose acetate having an acetyl content of 39.8%, 40 wt % of Copovidone VA64. A 1.0 mm exit orifice was drilled mechanically on the drug layer side of the dosage form. Residual solvents were removed by drying the dosage form at 40° C. and ambient humidity for 24 hours.

Figure 8:
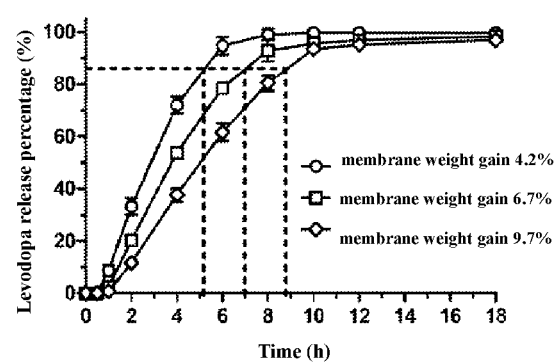
FIG. 8 shows the release profile of the UGI osmotic pump controlled-release drug delivery system described in Example 6.

As shown in FIG. 8, the dosage form delivered LD at an average rate of 38.3 mg/hr, 27.3 mg/hr, and 21.3 mg/hr, and the membrane weight gains were 4.2%, 6.7%, and 9.7%, respectively, with 85% of LD delivered in 5.0 hours, 7.0 hours and 9.0 hours.

EXAMPLE 7

Figure 9:
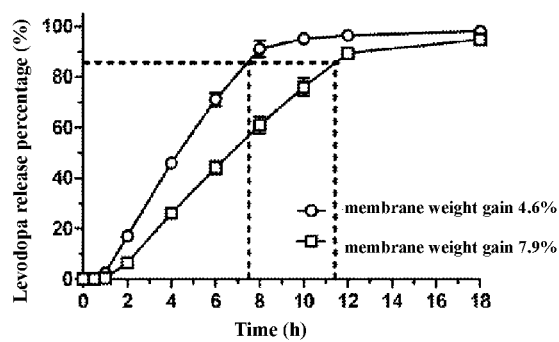
FIG. 9 shows the release profile of the UGI osmotic pump controlled-release drug delivery system described in Example 7.

The procedures of Example 6 were repeated in this example to provide the same dosage form except for the membrane-forming composition. In this example, the membrane-forming composition comprises, in weight percentage, 70 wt % of cellulose acetate with an acetyl content of 39.8%, and 30 wt % of Copovidone VA64. The membrane-forming composition was dissolved in a mixed solvent comprising 90% of acetone, 9.0% of ethanol, and 1.0% of deionized water to make a 4% of solid solution. As shown in FIG. 9, the dosage form having membrane weight gains of 4.6% and 7.9% delivered LD at an average rate of 25.5 mg/hr and 16.9 mg/hr, respectively, and correspondingly with 85% of LD delivered in 7.5 hours and 11.5 hours.

EXAMPLE 8

Figure 10:
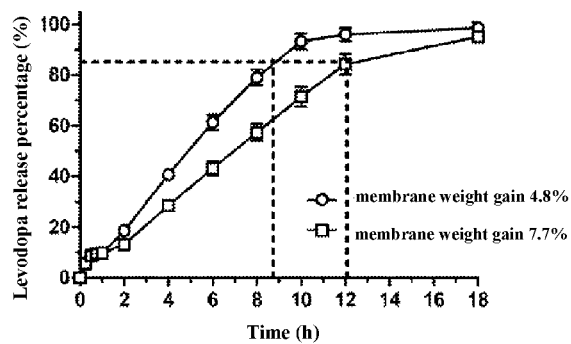
FIG. 10 shows the release profile of the UGI osmotic pump controlled-release drug delivery system described in Example 8.

The procedures of Example 7 were repeated in this example for providing a dosage form. In this example, the dried dosage forms with the membrane weight gains of 4.8% and 7.7% (as shown in FIG. 1.c) were overcoated with an immediate-release composition comprising 23.78 Wt % of levodopa, 64.22 Wt % of carbidopa, 10.0 Wt % of hydroxypropyl cellulose, 1.0 Wt % of aspartame and 1.0 Wt % of Mint flavor. The immediate-release overcoat composition was added to anhydrous ethanol to make a 10.0 Wt % of solid suspension. The final dosage form comprised an immediate-release coating comprising 62.5 mg of CD and 25 mg of LD, and a controlled-release drug layer comprising 225 mg of LD. As shown in FIG. 10, the release profile of the dosage form showed rapid release of LD/CD, followed by an extended release with a release duration of approximately 8.5 hours and 12.0 hours, respectively. The osmotic delivery system having a membrane weight gain of 4.8% can be kept in oral cavity for 4-5 hours, and then kept in oral cavity at meal time or for the whole release duration. The osmotic delivery system having a membrane weight gain of 7.7% can be kept in oral cavity for 8-9 hours before swallowed, or kept in oral cavity for the whole release duration.

EXAMPLE 9

In this example, the procedures of Example 1 were repeated, and the dosage form comprised a drug layer and a membrane-forming composition were identical to those provided in example 1. The drug layer comprised, in weight percentage, 38.0 Wt % of levodopa, 50.0 Wt % of microcrystalline cellulose, 2.0 Wt % of magnesium stearate and 10.0 Wt % of hydroxypropyl methylcellulose. The coating membrane comprised 50 Wt % of acetyl acetate membrane with an acetyl content of 39.8% and 50 Wt % of Copovidone VA64. In this example, the membrane weight gain was 4.50%. The final manufactured dosage form delivered levodopa at an average rate of 9.4 mg/hr, with 85% of levodopa delivered in 9.0 hours.

EXAMPLE 10

In this example, the procedures of Example 1 were repeated, and the dosage form comprised a drug layer and a membrane-forming composition were identical to those provided in example 1. The drug pull-layer comprised, in weight percentage, 19.5 Wt % of levodopa, 20.0 Wt % of carbidopa, 50.0 Wt % of mannitol and 10.0 Wt % of citric acid. The coating membrane comprised 50 Wt % of acetyl acetate membrane with an acetyl content of 39.8% and 50 Wt % of Copovidone VA64. In this example, the membrane weight gain was 4.50%. The final manufactured dosage form delivered levodopa at an average rate of 22.9 mg/hr, with 85% of levodopa delivered in 13.0 hours.

EXAMPLE 11

In this example, the procedures of Example 2 were repeated, and the dosage form comprised a drug layer, an osmosis layer and a membrane-forming composition were identical to those provided in example 2. The drug layer comprised, in weight percentage, 70.0 Wt % of levodopa, 9.0 Wt % of mannitol, 20.0% of Povidone K30 and 1.0 Wt % of magnesium stearate. The osmosis layer comprised, in weight percentage, 85.0 Wt % of sodium carboxymethyl cellulose (7H4XF), 3.0 Wt % of Povidone K30, 5.0 Wt % of sorbitol, 5.0 Wt % of iron oxide red and 2.0 Wt % of magnesium stearate. The coating membrane comprised, in weight percentage, 70 Wt % of acetyl acetate membrane with an acetyl content of 39.8% and 30 Wt % of Copovidone VA64. In this example, the membrane weight gain was 4.5%. The final manufactured dosage form delivered levodopa at an average rate of 35.0 mg/hr, with 85% of levodopa delivered in 8.5 hours.

EXAMPLE 12

In this example, the procedures of Example 2 were repeated, and the dosage form comprised a drug layer, an osmosis layer and a membrane-forming composition were identical to those provided in example 2. The drug layer comprised, in weight percentage, 20.0 Wt % of levodopa, 20.0 Wt % of carbidopa, 50.0 Wt % of hydroxypropyl cellulose, 4.0 Wt % of mannitol, 5.0 Wt % of aspartame and 1.0 Wt % of magnesium stearate. The osmosis layer comprised, in weight percentage, 25.0 Wt % of sodium carboxymethyl cellulose (7H4XF), 9.5 Wt % of Povidone K30, 65.0 Wt % of sorbitol and 0.5 Wt % of magnesium stearate. The coating membrane comprised, in weight percentage, 90 Wt % of acetyl acetate membrane with an acetyl content of 39.8% and 10 Wt % of Copovidone VA64. In this example, the membrane weight gain was 4.5%. The final manufactured dosage form delivered levodopa and CD at an average rate of 7.1 mg/hr, with 85% of levodopa/CD delivered in 12 hours.

EXAMPLE 13

In this example, the procedures of Example 8 were repeated, and the dosage form comprised a drug layer, an osmosis layer, a membrane-forming composition and an overcoat were identical to those provided in example 8. The drug layer comprised, in weight percentage, 45.0 Wt % of levodopa, 31.0 Wt % of hydroxypropyl cellulose, 17.0 Wt % of mannitol, 5.0 Wt % of Povidone K30, 1.0 Wt % of magnesium stearate and 1.0 Wt % of aspartame. The osmosis layer comprised, in weight percentage, 60.0 Wt % of sodium carboxymethyl cellulose (7H4XF), 10.0 Wt % of Povidone K30, 26.0 Wt % of sorbitol, 2.0 Wt % of iron oxide red and 2.0 Wt % of magnesium stearate. The coating membrane comprised, in weight percentage, 70 Wt % of acetyl acetate membrane with an acetyl content of 39.8% and 30 Wt % of Copovidone VA64. The weight of the coating membrane was 4.5% of the mass of the tablet core. The immediate-release overcoat comprised, in weight percentage, 93.0 Wt % of CD, 2.0 Wt % of hydroxypropyl cellulose EF and 5.0 Wt % of aspartame; the mass of the overcoat was 13.2% of the mass of the tablet core (table core+first layer coating membrane comprising cellulose acetate and Copovidone VA64). The immediate-release overcoat of the dosage form was first released rapidly, followed by an extended release with a release duration of approximately 8 hours. The osmotic delivery system can be kept in oral cavity for 4-5 hours and then swallowed before meal time or kept in oral cavity for the whole release duration.

EXAMPLE 14

In this example, the procedures of Example 8 were repeated, and the dosage form comprised a drug layer, an osmosis layer, a membrane-forming composition and an overcoat were identical to those provided in example 8. The drug layer comprised, in weight percentage, 45.0 Wt % of levodopa, 31.0 Wt % of hydroxypropyl cellulose, 12.0 Wt % of mannitol, 5.0 Wt % of Povidone K30, 5.0 Wt % of Mint flavor, 1.0 Wt % of magnesium stearate and 1.0 Wt % of aspartame. The osmosis layer comprised, in weight percentage, 40.0 Wt % of sodium carboxymethyl cellulose (7H4XF), 20.0 Wt % of Povidone K30, 36.0 Wt % of sorbitol, 3.5 Wt % of iron oxide red and 0.5 Wt % of magnesium stearate. The coating membrane comprised, in weight percentage, 70 Wt % of acetyl acetate membrane with an acetyl content of 39.8% and 30 Wt % of Copovidone VA64. The weight of the coating membrane was 4.5% of the mass of the tablet core. The immediate-release overcoat comprised, in weight percentage, 75.0 Wt % of LD, 20.0 Wt % of hydroxypropyl cellulose and 5.0 Wt % Mint flavor; the mass of the overcoat was 13.2% of the mass of the tablet core (table core+first layer coating membrane comprising cellulose acetate and Copovidone VA64). The immediate-release overcoat of the dosage form was first released rapidly, followed by an extended release with a release duration of approximately 8 hours. The osmotic delivery system can be kept in oral cavity for 4-5 hours and then be swallowed before meal time or kept in oral cavity for the whole release duration.

EXAMPLE 15

In this example, the procedures of Example 8 were repeated, and the dosage form comprised a drug layer, an osmosis layer, a membrane-forming composition and an overcoat were identical to those provided in example 8. The drug layer comprised, in weight percentage, 45.0 Wt % of levodopa, 31.0 Wt % of hydroxypropyl cellulose, 17.0 Wt % of mannitol, 5.0 Wt % of Povidone K30, 1.0 Wt % magnesium stearate and 1.0 Wt % of aspartame. The osmosis layer comprised, in weight percentage, 55.0 Wt % of sodium carboxymethyl cellulose (7H4XF), 10.0 Wt % of hydroxypropyl cellulose, 34.0 Wt % sorbitol, 0.5 Wt % of iron oxide red and 0.5 Wt % of magnesium stearate. The coating membrane comprised, in weight percentage, 70 Wt % of acetyl acetate membrane with an acetyl content of 39.8% and 30 Wt % of Copovidone VA64. The weight of the coating membrane was 5.9% of the mass of the tablet core. The solid content of the immediate-release overcoat suspension was 10.0 Wt %, comprising, in weight percentage, 24.0 Wt % of levodopa, 65.0 Wt % of carbidopa monohydrate, 10.0 Wt % of hydroxypropyl cellulose and 1.0 Wt % of aspartame; the weight of the overcoat was 13.1% of the weight of the tablet core (table core+first layer coating membrane comprising cellulose acetate and Copovidone VA64). When the solvent for the overcoat suspension was anhydrous ethanol, the level of the carbidopa-related genotoxic impurity hydrazine in the obtained dosage form was 1.7 ppm, and the content of the carbidopa-related impurity dihydroxyphenylacetone (DHPA) was 0.21%. When the solvent of the coating liquid of the overcoat was purified water, the concentration of the solid suspension of the overcoat was 10.0 Wt %, comprising, in weight percentage, 24.0 Wt % of levodopa, 65.0 Wt % of carbidopa monohydrate, 10.0 Wt % of hydroxypropyl cellulose and 1.0 Wt % of aspartame; the content of the carbidopa-related genotoxic impurity hydrazine in the obtained dosage form was 3.8 ppm, and the content of the carbidopa-related impurity DHPA was 0.28%. The carbidopa-related genotoxic impurity hydrazine and impurity DHPA of the obtained dosage form when the solvent of the coating liquid of the overcoat was anhydrous ethanol, were significantly lower than those of the obtained dosage form when the solvent of the coating liquid was purified water. The immediate-release overcoat of the dosage form was first released rapidly, followed by a sustained release with a duration of approximately 8 hours. The dosage form can be held in the oral cavity for 3-5 hours, and then be swallowed before meal time or kept in oral cavity for the whole release duration.

EXAMPLE 16

Firstly, a drug layer composition comprising 45.0 Wt % of levodopa, 31.0 Wt % of hydroxypropyl cellulose, 22.0 Wt % of mannitol, 0.9 Wt % of aspartame, 0.1 Wt % of Mint flavor and 0.5 Wt % of magnesium stearate was prepared, the components were each passed through a 40-mesh stainless steel sieve and granulated to obtain dry granules by a dry granulator, and then mixed with 0.5 Wt % of magnesium stearate.

Next, a second composition, an osmosis layer, comprising 55.0 Wt % of sodium carboxymethyl cellulose 7H4XF, 34.0 Wt % of sorbitol, 10.0 Wt % of hydroxypropyl cellulose and 0.5 Wt % of iron oxide red was prepared; the components were respectively passed through a 40-mesh stainless steel sieve and then dried to obtain dry granules by a dry granulator, and then mixed with 0.5 Wt % of magnesium stearate.

Next, the drug layer and osmotic layer granules were compressed into a bi-layer tablet core. First, 418 mg of drug layer granules were added to the 16×7 mm punch and tamped, and 209 mg of osmotic layer granules were added, then the two layers of granules were compressed into a contact bi-layer tablet core with a tablet press.

Next, the bi-layer tablet core was coated with a semi-permeable membrane. The membrane-forming composition comprised, in weight percentage, 70 Wt % of cellulose acetate with an acetyl content of 39.8 Wt %, and 30 Wt % of Copovidone VA64. The membrane-forming composition was dissolved in acetone to make a solution with 4% of solid content. Using the process parameters listed in Example 1, the membrane-forming composition was sprayed onto the bi-layer tablet core in a Glatt GC 1 pan coater to form a coating membrane, and the membrane weight gain of the coated tablet was 6.5%. Finally, a 1.0 mm exit orifice was drilled mechanically on the drug layer side of the dosage form.

Next, an immediate-release composition, comprising 54.0 Wt % of levodopa, 35.0 Wt % of carbidopa monohydrate, 10.0 Wt % of hydroxypropyl cellulose, 0.9 Wt % of aspartame and 0.1 Wt % of Mint flavor, was used to overcoat the dried dosage form, with the membrane weight gain of 6.5%. The immediate-release overcoat composition was added to anhydrous ethanol to make a 10.0 Wt % of solid suspension. The final dosage form was composed of an immediate-release overcoat comprising 62.5 mg of levodopa and 37.5 mg of carbidopa, and a controlled-release drug layer comprising 187.5 mg of levodopa.

The immediate-release overcoat of the dosage form was rapidly released first, followed by an extended release with a release duration of approximately 8 hours. The osmotic delivery system can be kept in oral cavity for 4-5 hours, and then was be swallowed before meal time or kept in oral cavity for the whole release duration.

EXAMPLE 17

In this example, the procedures of Example 16 were repeated, and the dosage form comprised a drug layer, an osmosis layer, a membrane-forming composition and an overcoat were all identical to those provided in example 16.

First, a drug layer composition comprising 45.0 Wt % of levodopa, 31.0 Wt % of hydroxypropyl cellulose, 22.0 Wt % of mannitol, 0.9 Wt % of aspartame, 0.1 Wt % of Mint flavor and 0.5 Wt % of magnesium stearate was prepared, the components were each passed through a 40-mesh stainless steel sieve, and dried to obtain dry granules by a dry granulator, then mixed with 0.5 Wt % of magnesium stearate.

Next, a second composition, i.e. an osmosis layer, comprising 55.0 Wt % of sodium carboxymethyl cellulose 7H4XF, 34.0 Wt % of sorbitol, 10.0 Wt % of hydroxypropyl cellulose and 0.5 Wt % of iron oxide red was prepared; the components were each passed through a 40-mesh stainless steel sieve, and dried to obtain dry granules by a dry granulator, then mixed with 0.5 Wt % of magnesium stearate.

Next, the drug layer and osmotic layer granules were compressed into a bi-layer tablet core. Firstly, 250 mg of drug layer granules were added to a 9 mm round punch of a tablet press and tamped, then 125 mg of osmotic layer granules were added to the punch, and the two layers of granules were compressed with a tablet press into a contact bi-layer tablet core.

Next, the bi-layer tablet core was coated with a semi-permeable membrane. The membrane-forming composition comprised, in weight percentage, 70 Wt % of cellulose acetate with an acetyl content of 39.8 Wt %, and 30 Wt % of Copovidone VA64. The membrane-forming composition was dissolved in acetone to make a 4% of solid solution. Using the process parameters listed in Example 1, the membrane-forming composition was sprayed onto the bi-layer tablet core in a Glatt GC 1 pan coater to form a coating membrane, and the membrane weight gain of the coated tablet was 7.0%. Finally, a 0.75 mm exit orifice was drilled mechanically on the drug layer side of the dosage form.

Next, an immediate-release composition, comprising 42.8 Wt % of levodopa, 46.2 Wt % of carbidopa monohydrate, 10.0 Wt % of hydroxypropyl cellulose, 0.9 Wt % of aspartame and 0.1 Wt % of Mint flavor, was used to overcoat the dried dosage form, with the membrane weight gain of 7.0%. The immediate-release overcoat composition was added to anhydrous ethanol to make a 10.0 Wt % of solid suspension. The final dosage form was composed of an immediate-release overcoat comprising 37.5 mg of levodopa and 37.5 mg of carbidopa, and a controlled-release drug layer comprising 112.5 mg of levodopa.

The immediate-release overcoat of the dosage form was rapidly released first, followed by an extended release with a release duration of approximately 8 hours. The osmotic delivery system can be kept in oral cavity for 4-5 hours, and then be swallowed before meal time or kept in oral cavity for the whole release duration.

EXAMPLE 18

In this example, the procedures of Example 16 were repeated, and the dosage form comprised a drug layer, an osmosis layer, a membrane-forming composition and an overcoat were identical to those provided in example 16.

First, a drug layer composition comprising 45.0 Wt % of levodopa, 31.0 Wt % of hydroxypropyl cellulose, 22.0 Wt % of mannitol, 0.9 Wt % of aspartame, 0.1 Wt % of Mint flavor and 0.5 Wt % of magnesium stearate was prepared, the components were each passed through a 40-mesh stainless steel sieve, and dried to obtain dry granules by a dry granulator, then mixed with 0.5 Wt % of magnesium stearate.

Next, a second composition, i.e. an osmosis layer, comprising 55.0 Wt % of sodium carboxymethyl cellulose 7H4XF, 34.0 Wt % of sorbitol, 10.0 Wt % of hydroxypropyl cellulose and 0.5 Wt % of iron oxide red was prepared; the components were each passed through a 40-mesh stainless steel sieve, and dried to obtain dry granules by a dry granulator, then mixed with 0.5 Wt % of magnesium stearate.

Next, the drug layer and osmotic layer granules were compressed into a bi-layer tablet core. Firstly, 125 mg of drug layer granules were added to a 7 mm round punch of a tablet press and tamped, then 62.5 mg of osmotic layer granules were added to the punch, and the two layers of granules were compressed into a contact bi-layer tablet core with a tablet press.

Next, the bi-layer tablet core was coated with a semipermeable membrane. The membrane-forming composition comprised, in weight percentage, 70 Wt % of cellulose acetate with an acetyl content of 39.8 Wt %, and 30 Wt % of Copovidone VA64. The membrane-forming composition was dissolved in acetone to make a 4% of solid solution. Using the process parameters listed in Example 1, the membrane-forming composition was sprayed onto the bi-layer tablet core in a Glatt GC 1 pan coater to form a coating membrane, and the membrane weight gain of the coated tablet was 9.0%. Finally, a 0.5 mm exit orifice was drilled mechanically on the drug layer side of the dosage form.

Next, an immediate-release composition comprising 28.2 Wt % of levodopa, 60.8 Wt % of carbidopa monohydrate, 10.0 Wt % of hydroxypropyl cellulose, 0.9 Wt % of aspartame and 0.1 Wt % of Mint flavor, was used to overcoat the dried dosage form, with a membrane weight gain of 9.0%. The immediate-release overcoat composition was added to anhydrous ethanol to make a 10.0 Wt % of solid suspension. The final dosage form comprised an immediate-release overcoat comprising 18.75 mg of levodopa and 37.5 mg of carbidopa, and a controlled-release drug layer comprising 56.25 mg of levodopa.

The immediate-release overcoat of the dosage form was rapidly released first, followed by an extended release with a release duration of approximately 8 hours. The osmotic delivery system can be kept in oral cavity for 4-5 hours, and then was be swallowed before meal time or kept in oral cavity for the whole release duration.

Although the specific embodiments of the present invention are described above, those skilled in the art should understand that these are merely examples, and that various changes or modifications may be made to these embodiments without departing from the principle and essence of the present invention. Therefore, the protection scope of the present invention is defined by the appended claims.

What we claim are:

1. A method that can provide a prolonged plasma concentration of an active pharmaceutical ingredient (API) with its absorption window limited at the upper gastrointestinal tract comprising administering to the individual an osmotic pump controlled-release system comprising a pharmaceutical composition, wherein the pharmaceutical composition comprises a tablet core comprising a drug pull-layer, an osmotic push-layer, and a coating membrane comprising cellulose acetate and copovidone, the weight of the cellulose acetate is 50-90% of the weight of the coating membrane; and the weight of the copovidone is 10-50% of the weight of the coating membrane;

wherein the copovidone is prepared by the following method comprising the following steps: polymerizing vinyl pyrrolidone and vinyl acetate, wherein the molar ratio of the vinyl pyrrolidone and vinyl acetate is 40:60-80:20;

wherein the drug pull-layer comprises the active pharmaceutical ingredient and excipients, and the active pharmaceutical ingredient comprises one or more of levodopa and carbidopa; and wherein the osmotic push-layer comprises a hydrophilic polymer, an osmotic agent, and a binding agent.

2. The method according to claim 1, wherein, the osmotic pump controlled-release system is kept in the oral cavity for 0-17 hours or 2-9 hours; or the molar ratio of the vinyl pyrrolidone and the vinyl acetate is 50:50-70:30 in the method for preparing the copovidone; or the excipients are one or more of a filler, an osmotic agent, a hydrophilic polymer, a binding agent, a lubricant, a preservative, a flavoring agent, an acidifying agent, and an antioxidant; or when the pharmaceutically active ingredients comprise levodopa, the weight percentage of the levodopa is 20-70%; when the active ingredients comprise carbidopa, the weight percentage of the carbidopa is 0-20% but not 0%; wherein the weight percentage is the weight percentage of each component of the drug pull-layer; or the coating membrane is composed of 50% weight percentage of cellulose acetate membrane and 50% weight percentage of copovidone VA64; the coating membrane is composed of 70% weight percentage of cellulose acetate membrane and 30% weight percentage of copovidone VA64; the coating membrane is composed weight percentage of 60% cellulose acetate membrane and 40% weight percentage of copovidone VA64; or the coating membrane is composed of 90% weight percentage of cellulose acetate membrane and 10% weight percentage of copovidone VA64; wherein the weight percentage is the weight percentage of each component of the coating membrane; or the weight of the coating membrane is not less than 2.0% of the weight of tablet core; or the coating membrane has one or more exit orifices with diameter of 0.5 mm-1.0 mm.

3. The method according to claim 2, wherein, the osmotic pump controlled-release system is kept in the oral cavity for the time 3-4 hours less than the release duration of at least 85% of active pharmaceutical ingredients of the pharmaceutical composition, then swallow the osmotic pump controlled-release system; or the molar ratio of the vinyl pyrrolidone and the vinyl acetate is 60:40 in the method for preparing the copovidone; or the excipients are one or more of a filler, an osmotic agent, a hydrophilic polymer, a binding agent, a lubricant, and a preservative; or when the pharmaceutically active ingredients comprise levodopa, the weight percentage of the levodopa is 35-55%; when the active ingredients comprise carbidopa, the weight percentage of the carbidopa is 5-15%; wherein the weight percentage is the weight percentage of each component of the drug pull-layer; or the weight of the coating membrane is 2.0-15.0% or 4.0-8.0% of the weight of tablet core; or the coating membrane has one or more exit orifices with diameter of 0.5 mm, 0.75 mm and 1.0 mm.

4. The method according to claim 2, wherein,
when the excipients comprise a filler, the filler is one or more of microcrystalline cellulose, hydroxypropyl cellulose, and mannitol, wherein the weight percentage of the filler is 0-50% but not 0%; or
when the excipients comprise an osmotic agent, the osmotic agent is one or more of magnesium sulfate, magnesium chloride, sodium chloride, lithium chloride, potassium sulfate, sodium sulfate, mannitol, urea, sorbitol, inositol, sucrose, and glucose, wherein the weight percentage of the osmotic agent is 0-50% but not 0%; or
when the excipients comprise a hydrophilic polymer, the hydrophilic polymer is one or more of hydroxypropyl cellulose, hydroxypropyl methylcellulose, carboxymethyl cellulose, polyvinylpyrrolidone, and hydroxyethyl cellulose, wherein the weight percentage of the hydrophilic polymer is 0-50% but not 0%; or
when the excipients comprise an acidifying agent, the acidifying agent is one or more of citric acid, sodium citrate, potassium citrate, malic acid, fumaric acid, lactic acid, phosphoric acid, and tartaric acid, wherein the weight percentage of the acidifying agent is 0-10% but not 0%;
wherein the weight percentage is the weight percentage of each component of the drug pull-layer.

5. The method according to claim 1, wherein, the osmotic push-layer comprises a hydrophilic polymer, an osmotic agent, a binding agent, and a lubricant; or the osmotic push-layer comprises a hydrophilic polymer, an osmotic agent, a binding agent, a lubricant, and a colorant.

6. The method according to claim 1, wherein,
the hydrophilic polymer in the osmotic push-layer is κ-carrageenan, sodium carboxymethyl cellulose, or polyethylene oxide, and the hydrophilic polymer has a molecular weight of 75,000-7,500,000 and a weight percentage 25-85%; or
the osmotic agent of the osmotic push-layer is one or more of magnesium sulfate, magnesium chloride, sodium chloride, lithium chloride, potassium sulfate, sodium sulfate, mannitol, urea, sorbitol, inositol, sucrose, and glucose, wherein the weight percentage of the osmotic agent is 5-65%; or
the binding agent is one or more of methyl cellulose, hydroxypropyl methylcellulose, hydroxypropyl cellulose, sodium carboxymethyl cellulose, povidone, and gelatin, wherein the weight percentage of the binding agent is 3-20%; or
the osmotic push-layer further comprises a lubricant, the lubricant is one or more of magnesium stearate, magnesium stearate fumarate, talc, and colloidal silica, wherein the weight percentage of the lubricant is 0-2% but not 0%; or
the osmotic push-layer further comprises a colorant, the colorant is one or more of iron oxide red, iron oxide yellow, and iron oxide black, wherein the weight percentage of the colorant is 0-5% but not 0%;
wherein the weight percentage is the weight percentage of each component of the osmotic push-layer.

7. The method according to claim 1, wherein, the osmotic push-layer comprises sodium carboxymethyl cellulose, povidone K30, sorbitol, and further comprises iron oxide red, and magnesium stearate; or the osmotic push-layer comprises sodium carboxymethyl cellulose, hydroxypropyl cellulose, sorbitol, and further comprises iron oxide red, and magnesium stearate.

8. The method according to claim 1, wherein the coating membrane is further covered with an overcoat.

9. The method according to claim 8, wherein the overcoat comprises active pharmaceutical ingredients and excipients, the active pharmaceutical ingredients comprise levodopa and/or carbidopa, and the excipients are one or more of hydroxypropyl cellulose, aspartame, and mint flavor; or
the overcoat weight gain of the tablet core is 12.9%, 13.2%, or 13.1% by weight.

10. The method according to claim 9, wherein,
when the active pharmaceutical ingredient is levodopa, the weight percentage of the levodopa is 0-75% but not 0%; or
when the active pharmaceutical ingredient is carbidopa, the weight percentage of carbidopa is 0-93% but not 0%; or
when the excipient of the overcoat comprises hydroxypropyl cellulose, the weight percentage of hydroxypropyl cellulose is 2-20%; or
when the excipient of the overcoat comprises aspartame, the weight percentage of the aspartame is 0-5% but not 0%; or
when the excipient of the overcoat comprises mint flavor, the weight percentage of the mint flavor is 0-5% but not 0%;
wherein the weight percentage is the weight percentage of each component of the overcoat.

11. The method according to claim 8, wherein
the drug pull-layer comprises levodopa, carbidopa, microcrystalline cellulose, mannitol, citric acid, sodium hydroxypropyl methylcellulose, and magnesium stearate; or
the drug pull-layer comprises levodopa, microcrystalline cellulose, hydroxypropyl methylcellulose, and magnesium stearate; or levodopa, carbidopa, mannitol, citric acid, and magnesium stearate; or
the drug pull-layer comprises levodopa, carbidopa, hydroxypropyl cellulose, mannitol, citric acid, and magnesium stearate; or
the drug pull-layer comprises levodopa, carbidopa, hydroxypropyl cellulose, mannitol, citric acid, and povidone K30; or
the drug pull-layer comprises levodopa, hydroxypropyl cellulose, mannitol, povidone K30, magnesium stearate, mint flavor, and aspartame; or
the drug pull-layer comprises levodopa, mannitol, povidone K30, and magnesium stearate; or
the drug pull-layer comprises levodopa, carbidopa, hydroxypropyl cellulose, mannitol, aspartame, and magnesium stearate; or
the drug pull-layer comprises levodopa, hydroxypropyl cellulose, mannitol, magnesium stearate, mint flavor, and aspartame; or
the drug pull-layer comprises levodopa, hydroxypropyl cellulose, mannitol, povidone K30, magnesium stearate, and aspartame; or
the osmotic push-layer comprises sodium carboxymethyl cellulose, povidone K30, sorbitol, iron oxide red and magnesium stearate; or
the overcoat comprises levodopa, carbidopa, hydroxypropyl cellulose, aspartame, and mint flavor; levodopa, carbidopa, hydroxypropyl cellulose, and aspartame; or
the overcoat comprises carbidopa, hydroxypropyl cellulose, and aspartame; or the overcoat comprises levodopa, hydroxypropyl cellulose, and mint flavor.

12. The method according to claim 11, wherein
the drug pull-layer is composed of levodopa, carbidopa, microcrystalline cellulose, mannitol, citric acid, sodium hydroxypropyl methylcellulose, and magnesium stearate, the weight percentage of the levodopa is 40%, the weight percentage of the carbidopa is 10.8%, the weight percentage of the microcrystalline cellulose is 20%, the weight percentage of the mannitol is 18.7%, the weight percentage of the citric acid is 5%, the weight percentage of the sodium hydroxypropyl methylcellulose is 5%, and the weight percentage of the magnesium stearate is 0.5%, wherein the weight percentage is the weight percentage of each component of the drug pull-layer; or the drug pull-layer is composed of levodopa, microcrystalline cellulose, hydroxypropyl methylcellulose, and magnesium stearate, the weight percentage of the levodopa is 38%, the weight percentage of the microcrystalline cellulose is 50%, the weight percentage of the hydroxypropyl methylcellulose is 10%, and the weight percentage of the magnesium stearate is 2%, wherein the weight percentage is the weight percentage of each component of the drug pull-layer; or the drug pull-layer is composed of levodopa, carbidopa, mannitol, citric acid, and magnesium stearate, the weight percentage of the levodopa is 19.5%, the weight percentage of the carbidopa is 20%, the weight percentage of the mannitol is 50%, the weight percentage of the citric acid is 10%, and the weight percentage of magnesium stearate is 0.5%, wherein the weight percentage is the weight percentage of each component of the drug pull-layer; or the drug pull-layer is composed of levodopa, carbidopa, hydroxypropyl cellulose, mannitol, citric acid, and magnesium stearate, the weight percentage of the levodopa is 40%, the weight percentage of the carbidopa is 10.8%, the weight percentage of the hydroxypropyl cellulose is 31%, the weight percentage of the mannitol is 12.7%, the weight percentage of the citric acid is 5%, and the weight percentage of the magnesium stearate is 0.5%, wherein the weight percentage is the weight percentage of each component of the drug pull-layer; or the drug pull-layer is composed of levodopa, carbidopa, hydroxypropyl cellulose, mannitol, citric acid, and povidone K30, the weight percentage of the levodopa is 40%, the weight percentage of the carbidopa is 10.8%, the weight percentage of the hydroxypropyl cellulose is 31%, the weight percentage of the mannitol is 12.7%, the weight percentage of the citric acid is 5% and the weight percentage of the povidone K30 is 0.5%, wherein the weight percentage is the weight percentage of each component of the drug pull-layer; or the drug pull-layer is composed of levodopa, hydroxypropyl cellulose, mannitol, povidone K30, magnesium stearate, mint flavor, and aspartame, the weight percentage of the levodopa is 45%, the weight percentage of the hydroxypropyl cellulose is 31%, the weight percentage of the mannitol is 16%, the weight percentage of the povidone K30 is 5%, the weight percentage of the magnesium stearate is 1%, the weight percentage of the mint flavor is 1% and the weight percentage of the aspartame is 1%, wherein the weight percentage is the weight percentage of each component of the drug pull-layer; or the drug pull-layer is composed of levodopa, mannitol, povidone K30, and magnesium stearate, the weight percentage of the levodopa is 70%, the weight percentage of the mannitol is 9%, the weight percentage of the povidone K30 is 20% and the weight percentage of the magnesium stearate is 1%, wherein the weight percentage is the weight percentage of each component of the drug pull-layer; or the drug pull-layer is composed of levodopa, carbidopa, hydroxypropyl cellulose, mannitol, aspartame, and magnesium stearate, the weight percentage of the levodopa is 20%, the weight percentage of the carbidopa is 20%, the weight percentage of the hydroxypropyl cellulose is 50%, the weight percentage of the mannitol is 4%, the weight percentage of the aspartame is 5% and the weight percentage of the magnesium stearate is 1%, wherein the weight percentage is the weight percentage of each component of the drug pull-layer; or the drug pull-layer is composed of levodopa, hydroxypropyl cellulose, mannitol, povidone K30, magnesium stearate, and aspartame, the weight percentage of the levodopa is 45%, the weight percentage of the hydroxypropyl cellulose is 31%, the weight percentage of the mannitol is 17%, the weight percentage of the povidone K30 is 5%, the weight percentage of the magnesium stearate is 1% and the weight percentage of the aspartame is 1%, wherein the weight percentage is the weight percentage of each component of the drug pull-layer; or the drug pull-layer is composed of levodopa, hydroxypropyl cellulose, mannitol, povidone K30, magnesium stearate, and aspartame, the weight percentage of the levodopa is 45%, the weight percentage of the hydroxypropyl cellulose is 31%, the weight percentage of the mannitol is 17%, the weight percentage of the povidone K30 is 5%, the weight percentage of the magnesium stearate is 1% and the weight percentage of the aspartame is 1%, wherein the weight percentage is the weight percentage of each component of the drug pull-layer; or the drug pull-layer is composed of levodopa, hydroxypropyl cellulose, mannitol, povidone K30, magnesium stearate, mint flavor, and aspartame, the weight percentage of the levodopa 45%, the weight percentage of the hydroxypropyl cellulose is 31%, the weight percentage of the mannitol is 12%, the weight percentage of the povidone K30 is 5%, and the weight percentage of the mint flavor is 5%, the weight percentage of the aspartame is 1% and the weight percentage of the magnesium stearate is 1%, wherein the weight percentage is the weight percentage of each component of the drug pull-layer; or the drug pull-layer is composed of levodopa, hydroxypropyl cellulose, mannitol, magnesium stearate, mint flavor, and aspartame, the drug pull-layer is composed of 45% weight percentage of levodopa, 31% weight percentage of hydroxypropyl cellulose, 22% weight percentage of mannitol, 0.9% weight percentage of aspartame, 1.0% weight percentage of magnesium stearate and 0.1% weight percentage of mint flavor; wherein the weight percentage is the weight percentage of each component of the drug pull-layer; or the osmotic push-layer is composed of sodium carboxymethyl cellulose 7H4XF, povidone K30, sorbitol, iron oxide red, and magnesium stearate, the weight percentage of the sodium carboxymethyl cellulose 7H4XF is 55%, the weight percentage of the povidone K30 is 5%, the weight percentage of sorbitol is 39%, the weight percentage of the iron oxide red is 0.5% and the weight percentage of the magnesium stearate is 0.5%, wherein the weight percentage is the weight percentage of each component of the osmotic push-layer; or the osmotic push-layer is composed of sodium carboxymethyl cellulose 7H4XF, povidone K30, sorbitol, iron oxide red, and magnesium stearate, the weight percentage of the sodium carboxymethyl cellulose 7H4XF is 55%, the weight percentage of the povidone K30 is 10%, the weight percentage of the sorbitol is 34%, the weight percentage of the iron oxide red is 0.5% and the weight percentage of the magnesium stearate is 0.5%, wherein the weight percentage is the weight percentage of each component of the osmotic push-layer; or the osmotic push-layer is composed of sodium carboxymethyl cellulose 7H4XF, povidone K30, sorbitol, iron oxide red, and magnesium stearate, the weight percentage of the sodium carboxymethyl cellulose is 85%, the weight percentage of the povidone K30 is 3%, the weight percentage of the sorbitol is 5%, the weight percentage of the iron oxide red is 5% and the weight percentage of the magnesium stearate is 2%, wherein the weight percentage is the weight percentage of each component of the osmotic push-layer; or the osmotic push-layer is composed of sodium carboxymethyl cellulose 7H4XF, povidone K30, sorbitol, iron oxide red, and magnesium stearate, the weight percentage of the sodium carboxymethyl cellulose is 25%, the weight percentage of the povidone K30 is 9.5%, the weight percentage of the sorbitol is 65% and the weight percentage of the magnesium stearate is 0.5%, wherein the weight percentage is the weight percentage of each component of the osmotic push-layer; or the osmotic push-layer is composed of sodium carboxymethyl cellulose 7H4XF, povidone K30, sorbitol, iron oxide red, and magnesium stearate, the weight percentage of the sodium carboxymethyl cellulose 7H4XF is 60%, the weight percentage of the povidone K30 is 10%, the weight percentage of the sorbitol is 26%, the weight percentage of the iron oxide red is 2% and the weight percentage of the magnesium stearate is 2%, wherein the weight percentage is the weight percentage of each component of the osmotic push-layer; or the osmotic push-layer is composed of sodium carboxymethyl cellulose 7H4XF, povidone K30, sorbitol, iron oxide red, and magnesium stearate, the weight percentage of the sodium carboxymethyl cellulose 7H4XF is 40%, the weight percentage of the povidone K30 is 20%, the weight percentage of the sorbitol is 36%, the weight percentage of the iron oxide red is 3.5% and the weight percentage of the magnesium stearate is 0.5%, wherein the weight percentage is the weight percentage of each component of the osmotic push-layer; or the osmotic push-layer is composed of sodium carboxymethyl cellulose 9H4XF, povidone K30, sorbitol, iron oxide red, and magnesium stearate, the weight percentage of the sodium carboxymethyl cellulose 9H4XF is 55%, the weight percentage of the povidone K30 is 5%, the weight percentage of the sorbitol is 39%, the weight percentage of the iron oxide red is 0.5% and the weight percentage of the magnesium stearate is 0.5%, wherein the weight percentage is the weight percentage of each component of the osmotic push-layer; or the osmotic push-layer is composed of sodium carboxymethyl cellulose 7H4XF, hydroxypropyl cellulose, sorbitol, iron oxide red, and magnesium stearate, the weight percentage of the sodium carboxymethyl cellulose is 55%, the weight percentage of the hydroxypropyl cellulose is 10%, the weight percentage of the sorbitol is 34%, the weight percentage of the iron oxide red is 0.5% and the weight percentage of the magnesium stearate is 0.5%, wherein the weight percentage is the weight percentage of each component of the osmotic push-layer; or the overcoat is composed of levodopa, carbidopa, hydroxypropyl cellulose, aspartame, and mint flavor, the weight percentage of the levodopa is 23.78%, the weight percentage of the carbidopa is 64.22%, the weight percentage of the hydroxypropyl cellulose is 10%, the weight percentage of the aspartame is 1% and the weight percentage of mint flavor is 1%, wherein the weight percentage is the weight percentage of each component of the overcoat; or the overcoat is composed of carbidopa, hydroxypropyl cellulose, and aspartame, the weight percentage of the carbidopa is 93%, the weight percentage of the hydroxypropyl cellulose is 2% and the weight percentage of the aspartame is 5%, wherein the weight percentage is the weight percentage of each component of the overcoat; or the overcoat is composed of levodopa, hydroxypropyl cellulose, and mint flavor, the weight percentage of the levodopa is 75%, the weight percentage of the hydroxypropyl cellulose is 20% and the weight percentage of the mint flavor is 5%, wherein the weight percentage is the weight percentage of each component of the overcoat; or the overcoat is composed of levodopa, carbidopa, hydroxypropyl cellulose, and aspartame, the weight percentage of the levodopa is 24%, the weight percentage of the carbidopa is 65%, the weight percentage of the hydroxypropyl cellulose is 10% and the weight percentage of the aspartame is 1%, wherein the weight percentage is the weight percentage of each component of the overcoat; or the overcoat is composed of levodopa, carbidopa, hydroxypropyl cellulose, aspartame, and mint flavor, the weight percentage of the levodopa is 54%, the weight percentage of the carbidopa is 35%, the weight percentage of the hydroxypropyl cellulose is 10%, the weight percentage of the aspartame is 0.9%, the weight percentage of mint flavor is 0.1%; or the overcoat is composed of levodopa, carbidopa, hydroxypropyl cellulose, aspartame, and mint flavor, the weight percentage of the levodopa is 42.8%, the weight percentage of the carbidopa is 46.2%, the weight percentage of the hydroxypropyl cellulose is 10%, the weight percentage of the aspartame is 0.9%, the weight percentage of the mint flavor is 0.1%; wherein the weight percentage is the weight percentage of each component of the overcoat.

13. The method according to claim 11, wherein the pharmaceutical composition is composed of a drug pull-layer, an osmotic push-layer, and a coating membrane, wherein the drug pull-layer is composed of 40% weight percentage of levodopa, 10.8% weight percentage of carbidopa, 31% weight percentage of hydroxypropyl cellulose, 12.7% weight percentage of mannitol, 5% weight percentage of citric acid and 0.5% weight percentage of magnesium stearate; wherein the weight percentage is its weight percentage of the drug pull-layer; the osmotic push-layer is composed of 55% weight percentage of sodium carboxymethyl cellulose 7H4XF or 9H4XF, 5% weight percentage of povidone K30, 39% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% weight percentage of cellulose acetate membrane and 30% weight percentage of copovidone VA64, wherein the weight percentage is its weight percentage of the coating membrane; and the weight of the coating membrane is 2.0%, 4.0%, or 5.0% of the weight of the tablet core; or the pharmaceutical composition is composed of a drug pull-layer, an osmotic push-layer, and a coating membrane, wherein the drug pull-layer is composed of 40% weight percentage of levodopa, 10.8% weight percentage of carbidopa, 31% weight percentage of hydroxypropyl cellulose, 12.7% weight percentage of mannitol, 5% weight percentage of citric acid and 0.5% weight percentage of povidone K30, wherein the weight percentage is its weight percentage of the drug pull-layer; the osmotic push-layer is composed of 55% weight percentage of sodium carboxymethyl cellulose 7H4XF, 5% weight percentage of povidone K30, 39% weight percentage of sorbitol, 0.5% weight percentage of iron oxide red and 0.5% weight percentage of magnesium stearate, wherein the weight percentage is its weight percentage of the osmotic push-layer; the coating membrane is composed of 60% weight percentage of cellulose acetate membrane and 40% weight percentage of copovidone VA64, wherein the weight percentage is its weight percentage of the coating membrane; and the weight of the coating membrane is 5.0% of the weight of the tablet core; or the pharmaceutical composition is composed of a drug pull-layer, an osmotic push-layer, and a coating membrane, wherein the drug pull-layer is composed of 45% weight percentage of levodopa, 31% weight percentage of hydroxypropyl cellulose, 16% weight percentage of mannitol, 5% weight percentage of povidone K30, 1% weight percentage of magnesium stearate, 1% weight percentage of mint flavor and 1% weight percentage of aspartame, wherein the weight percentage is its weight percentage of the drug pull-layer; the osmotic push-layer is composed of 55% weight percentage of sodium carboxymethyl cellulose 7H4XF, 10% weight percentage of povidone K30, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 60% weight percentage of cellulose acetate membrane and 40% weight percentage of copovidone VA64, wherein the weight percentage is its weight percentage of the coating membrane; and the weight of the coating membrane is 4.2%, 6.7% or 9.7% of the weight of the tablet core; or the pharmaceutical composition is composed of a drug pull-layer, an osmotic push-layer, and a coating membrane, wherein the drug pull-layer is composed of 45% weight percentage of levodopa, 31% weight percentage of hydroxymethyl cellulose, 16% weight percentage of mannitol, 5% weight percentage of povidone K30, 1% weight percentage of magnesium stearate, 1% weight percentage of mint flavor and 1% weight percentage of aspartame, wherein the weight percentage is its weight percentage of the drug pull-layer; the osmotic push-layer is composed of 55% weight percentage of sodium carboxymethyl cellulose 7H4XF, 10% weight percentage of povidone K30, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% weight percentage of cellulose acetate membrane and 30% weight percentage of copovidone VA64, wherein the weight percentage is its weight percentage of the coating membrane; and the weight of the coating membrane is 4.6% or 7.9% of the weight of the tablet core; or the pharmaceutical composition is composed of a drug pull-layer, an osmotic push-layer, and a coating membrane, wherein the drug pull-layer is composed of 70% weight percentage of levodopa, 9% weight percentage of mannitol, 20% weight percentage of povidone K30 and 1% weight percentage of magnesium stearate, wherein the weight percentage is its weight percentage of the drug pull-layer; the osmotic push-layer is composed of 85% weight percentage of sodium carboxymethyl cellulose, 3% weight percentage of povidone K30, 5% weight percentage of sorbitol, 5% weight percentage of iron oxide red and 2% weight percentage of magnesium stearate, wherein the weight percentage is its weight percentage of the osmotic push-layer; the coating membrane is composed of 70% weight percentage of cellulose acetate membrane and 30% weight percentage of copovidone VA64, wherein the weight percentage is its weight percentage of the coating membrane; and the weight of the coating membrane is 4.5% of the weight of the tablet core; or the pharmaceutical composition is composed of a drug pull-layer, an osmotic push-layer, and a coating membrane, wherein the drug pull-layer is composed of 20% weight percentage of levodopa, 20% weight percentage of carbidopa, 50% weight percentage of hydroxypropyl cellulose, 4% weight percentage of mannitol, 5% weight percentage of aspartame and 1% weight percentage of magnesium stearate, wherein the weight percentage is its weight percentage of the drug pull-layer; the osmotic push-layer is composed of 25% weight percentage of sodium carboxymethyl cellulose, 9.5% weight percentage of povidone K30, 65% weight percentage of sorbitol and 0.5% weight percentage of magnesium stearate, wherein the weight percentage is its weight percentage of the osmotic push-layer; the coating membrane is composed of 90% weight percentage of cellulose acetate membrane and 10% weight percentage of copovidone VA64, wherein the weight percentage is its weight percentage of the coating membrane; and the weight of the coating membrane is 4.5% of the weight of the tablet core; or the pharmaceutical composition is composed of a drug pull-layer, an osmotic push-layer, a coating membrane, and an overcoat, wherein the drug pull-layer is composed of 45% weight percentage of levodopa, 31% weight percentage of hydroxypropyl cellulose, 16% weight percentage of mannitol, 5% weight percentage of povidone K30, 1% weight percentage of magnesium stearate, 1% weight percentage of mint flavor and 1% weight percentage of aspartame, wherein the weight percentage is its weight percentage of the drug pull-layer; the osmotic push-layer is composed of 55% weight percentage of sodium carboxymethyl cellulose 7H4XF, 10% weight percentage of povidone K30, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% weight percentage of cellulose acetate membrane and 30% weight percentage of copovidone VA64, the weight percentage is its weight percentage of the coating membrane, and the weight of the coating membrane is 4.8% or 7.7% of the weight of the tablet core; the overcoat comprises an immediate-release composition comprising 23.78% weight percentage of levodopa, 64.22% weight percentage of carbidopa, 10% weight percentage of hydroxypropyl cellulose, 1% weight percentage of aspartame and 1% weight percentage of mint flavor, wherein the weight percentage is its weight percentage of the overcoat, and overcoat weight gains of the tablet core are 13.2% and 12.9%, respectively; or the pharmaceutical composition is composed of a drug pull-layer, an osmotic push-layer, a coating membrane, and an overcoat, wherein the drug pull-layer is composed of 45% weight percentage of levodopa, 31% weight percentage of hydroxypropyl cellulose, 17% weight percentage of mannitol, 5% weight percentage of povidone K30, 1% weight percentage of magnesium stearate and 1% weight percentage of aspartame, wherein the weight percentage is its weight percentage of the drug pull-layer; the osmotic push-layer is composed of 60% weight percentage of sodium carboxymethyl cellulose 7H4XF, 10% weight percentage of povidone K30, 26% weight percentage of sorbitol, 2% weight percentage of iron oxide red and 2% weight percentage of magnesium stearate, wherein, the weight percentage is its weight percentage of the osmotic push-layer; the coating membrane is composed of 70% weight percentage of cellulose acetate membrane and 30% weight percentage of copovidone VA64, wherein, the weight percentage is its weight percentage of the coating membrane, and the weight of the coating membrane is 4.8% of the weight of the tablet core; the overcoat comprises an immediate-release composition comprising 93% weight percentage of carbidopa, 2% weight percentage of hydroxypropyl cellulose and 5% weight percentage of aspartame, wherein, the weight percentage is its weight percentage of the overcoat, and overcoat weight gain of the tablet core is 13.2% weight percentage; or the pharmaceutical composition is composed of a drug pull-layer, an osmotic push-layer, a coating membrane, and an overcoat, wherein the drug pull-layer is composed of 45% weight percentage of levodopa, 31% weight percentage of hydroxypropyl cellulose, 12% weight percentage of mannitol, 5% weight percentage of povidone K30, 5% weight percentage of mint flavor, 1% weight percentage of aspartame and 1% weight percentage of magnesium stearate, wherein the weight percentage is its weight percentage of the drug pull-layer; the osmotic push-layer is composed of 40% weight percentage of sodium carboxymethyl cellulose 7H4XF, 20% weight percentage of povidone K30, 36% weight percentage of sorbitol, 3.5% weight percentage of iron oxide red and 0.5% weight percentage of magnesium stearate, wherein the weight percentage is its weight percentage of the osmotic push-layer; the coating membrane is composed of 70% weight percentage of cellulose acetate membrane and 30% weight percentage of copovidone VA64, wherein the weight percentage is its weight percentage of the coating membrane, and the weight of the coating membrane is 4.8% of the weight of the tablet core; the overcoat comprises an immediate-release composition comprising 75% weight percentage of levodopa, 20% weight percentage of hydroxypropyl cellulose and 5% weight percentage of mint flavor, wherein the weight percentage is its weight percentage of the overcoat, and overcoat weight gain of the tablet core is 13.2% weight percentage respectively; or the pharmaceutical composition is composed of a drug pull-layer, an osmotic the pharmaceutical composition is composed of a drug pull-layer, an osmotic push-layer, a coating membrane and an overcoat, wherein the drug pull-layer is composed of 45% weight percentage of levodopa, 31% weight percentage of hydroxymethyl cellulose, 17% weight percentage of mannitol, 5% weight percentage of povidone K30, 1% weight percentage of magnesium stearate and 1% weight percentage of aspartame, wherein the weight percentage is its weight percentage of the drug pull-layer; the osmotic push-layer is composed of 55% weight percentage of sodium carboxymethyl cellulose 7H4XF, 10% weight percentage of hydroxypropyl cellulose, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% weight percentage of cellulose acetate and 30% weight percentage of copovidone VA64, the weight percentage is its weight percentage of the coating membrane, wherein the cellulose acetate comprises 39.8 Wt % of acetyl acetate membrane, and the weight of the coating membrane is 5.9% of the weight of the tablet core; and, the overcoat is composed of 24% weight percentage of levodopa, 65% weight percentage of carbidopa, 10% weight percentage of hydroxypropyl cellulose and 1% weight percentage of aspartame, wherein the weight percentage is its weight percentage of the overcoat, and the weight of the overcoat is 13.1% of the total weight of the tablet core and the coating membrane; or the pharmaceutical composition is composed of a drug pull-layer, an osmotic push-layer, a coating membrane and an overcoat; wherein the drug pull-layer is composed of 45% weight percentage of levodopa, 31% weight percentage of hydroxypropyl cellulose, 22% weight percentage of mannitol, 0.9% weight percentage of aspartame, 1% weight percentage of magnesium stearate and 0.1% weight percentage of mint flavor, wherein the weight percentage is its weight percentage of the drug pull-layer; the osmotic push-layer is composed of 55% weight percentage of sodium carboxymethyl cellulose 7H4XF, 10% weight percentage of hydroxypropyl cellulose, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% of cellulose acetate and 30% of copovidone V64, wherein the weight percentage is its weight percentage of the coating membrane; wherein the cellulose acetate comprises 39.8 Wt % of acetyl acetate membrane, and the weight of the coating membrane is 6.5% of the weight of the tablet core; and, the overcoat is composed of 54% weight percentage of levodopa, 35% weight percentage of carbidopa, 10% weight percentage of hydroxypropyl cellulose and 0.9% weight percentage of aspartame and 0.1% weight percentage of mint flavor, wherein the weight percentage is its weight percentage of the overcoat; or the pharmaceutical composition is composed of a drug pull-layer, an osmotic push-layer, a coating membrane and an overcoat; wherein the drug pull-layer is composed of 45% weight percentage of levodopa, 31% weight percentage of hydroxypropyl cellulose, 22% weight percentage of mannitol, 0.9% weight percentage of aspartame, 1% weight percentage of magnesium stearate and 0.1% weight percentage of mint flavor, wherein the weight percentage is its weight percentage of the drug pull-layer: the osmotic push-layer is composed of 55% weight percentage of sodium carboxymethyl cellulose 7H4XF, 10% weight percentage of hydroxypropyl cellulose, 34% weight percentage of sorbitol, 0.5% weight percentage of iron oxide red and 0.5% weight percentage of magnesium stearate, the weight percentage is its weight percentage of the osmotic push-layer; the coating membrane is composed of 70% of cellulose acetate and 30% of copovidone V64, wherein the weight percentage is its weight percentage of the coating membrane; wherein the cellulose acetate comprises 39.8 Wt % of acetyl acetate membrane, and the weight of the coating membrane is 7.0% of the weight of the tablet core; and, the overcoat is composed of 42.8% weight percentage of levodopa, 46.2% weight percentage of carbidopa, 10% weight percentage of hydroxypropyl cellulose and 0.9% weight percentage of aspartame and 0.1% weight percentage of mint flavor, wherein the weight percentage is its weight percentage of the overcoat; or the pharmaceutical composition is composed of a drug pull-layer, an osmotic push-layer, a coating membrane, and an overcoat; wherein the drug pull-layer is composed of 45% weight percentage of levodopa, 31% weight percentage of hydroxypropyl cellulose, 22% weight percentage of mannitol, 0.9% weight percentage of aspartame, 1% weight percentage of magnesium stearate and 0.1% weight percentage of mint flavor, wherein the weight percentage is its weight percentage of the drug pull-layer: the osmotic push-layer is composed of 55% weight percentage of sodium carboxymethyl cellulose 7H4XF, 10% weight percentage of hydroxypropyl cellulose, 34% weight percentage of sorbitol, 0.5% weight percentage of iron oxide red and 0.5% weight percentage of magnesium stearate, wherein the weight percentage is its weight percentage of the osmotic push-layer; the coating membrane is composed of 70% of cellulose acetate and 30% of copovidone V64, wherein the weight percentage is its weight percentage of the coating membrane; wherein the cellulose acetate comprises 39.8 Wt % of acetyl acetate membrane, and the weight of the coating membrane is 9.0% of the weight of the tablet core; and, the overcoat is composed of 28.2% weight percentage of levodopa, 60.8% weight percentage of carbidopa, 10% weight percentage of hydroxypropyl cellulose and 0.9% weight percentage of aspartame and 0.1% weight percentage of mint flavor, wherein the weight percentage is its weight percentage of the overcoat.

14. An osmotic pump controlled-release drug delivery system comprising a pharmaceutical composition; wherein the pharmaceutical composition comprises a tablet core comprising a drug pull-layer, an osmotic push-layer, and a coating membrane comprising cellulose acetate and copovidone, the weight of the cellulose acetate is 50-90% of the weight of the coating membrane; and the weight of the copovidone is 10-50% of the weight of the coating membrane;

wherein the copovidone is prepared by the following method comprising the following steps: polymerizing vinyl pyrrolidone and vinyl acetate, wherein the molar ratio of the vinyl pyrrolidone and vinyl acetate is 40:60-80:20;

wherein the drug pull-layer comprises active pharmaceutical ingredients and excipients, and the active pharmaceutical ingredients comprises one or more of levodopa and carbidopa, and wherein the osmotic push-layer comprises a hydrophilic polymer, an osmotic agent, and a binding agent.

15. A method for preparing the osmotic pump controlled-release drug delivery system according to claim 14, comprising adopting the following method 1, method 2, or method 3;

method 1 comprises the following steps: coating the tablet core comprising the drug pull-layer with the coating membrane;

method 2 comprises the following steps: coating the tablet core comprising the drug pull-layer and the osmotic push-layer with the coating membrane; or method 3 comprises the following steps: coating the tablet core comprising the drug pull-layer and the osmotic push-layer with the coating membrane; and then overcoating the membrane-coated tablet with an overcoat.

16. An osmotic pump controlled-release drug delivery system prepared according to the method of claim 15.

17. The method for preparing the osmotic pump controlled-release drug delivery system according to claim 15, in the method 1, the method 2, and the method 3, the preparation of the tablet core includes the following steps:

(1) using wet or dry granulation to obtain drug pull-layer granules: the weight of the drug pull-layer is 125-500 mg, and the preparation of the coating membrane includes the following steps:

(1) dissolving the cellulose acetate and copovidone in acetone according to the weight percentage thereof;

(2) coating the tablet core with the solid solution obtained in the above step to form a coating membrane; and (3) drilling orifices on the coating membrane.

18. The method for preparing the osmotic pump controlled-release drug delivery system according to claim 17, in the method 2 and the method 3, the preparation of the tablet core further comprises the following steps:

(2) granulating to form osmotic push-layer granules: the weight of the osmotic push-layer is 62.5-250 mg; and (3) compressing the drug pull-layer granules and the osmotic push-layer granules into a bi-layer tablet core.

19. The method for preparing the osmotic pump controlled-release drug delivery system according to claim 18, in the method 3, the preparation of the overcoat comprises the following steps:

(1) dissolving the components of the overcoat in an alcohol solvent according to the weight percentage thereof to prepare an overcoat suspension; and (2) coating the drug overcoat suspension obtained in the above step to the membrane-coated tablet.

20. The method according to claim 7, wherein,
the sodium carboxymethyl cellulose is sodium carboxymethyl cellulose 7H4XF or 9H4XF; or,
the osmotic push-layer comprises 25-85% weight percentage of sodium carboxymethyl cellulose, 5-65% weight percentage of sorbitol, 3-20% weight percentage of povidone, and further comprises 0-5% weight percentage of iron oxide red and 0.5-2% weight percentage of magnesium stearate; or the osmotic push-layer comprises 25-85% weight percentage of sodium carboxymethyl cellulose, 5-65% weight percentage of sorbitol, 3-20% weight percentage of hydroxypropyl cellulose, and further comprises 0-5% weight percentage of iron oxide red and 0.5-2% weight percentage of magnesium stearate; wherein the weight percentage is the weight percentage of each component of the osmotic push-layer.

21. The osmotic pump controlled-release drug delivery system according to claim 14, wherein the osmotic pump controlled-release drug delivery system is a controlled-release tablet; and
the controlled-release tablet is a cylindrical shape with a diameter of 5-10 mm and a height of 5-30 mm, or a capsule shape with a length of 10-25 mm and a width of 5-10 mm.

* * * * *